US010589086B2

(12) United States Patent
Sacristan et al.

(10) Patent No.: US 10,589,086 B2
(45) Date of Patent: Mar. 17, 2020

(54) DEEP NERVE STIMULATOR

(71) Applicants: Nervive, Inc., Akron, OH (US); MEDINGENIUM S.A. DE C.V., Napoles (MX)

(72) Inventors: Emilio Sacristan, Tlalpan (MX); Douglas Stewart Szumski, New Milton Hampshire (GB); Jonathan Velleuer, Leipzig (DE); Judith Müller, Leipzig (DE); Mark Borsody, Orinda, CA (US)

(73) Assignee: NERVIVE, INC, Akron, OH (US)

( * ) Notice: Subject to any disclaimer, the term of this patent is extended or adjusted under 35 U.S.C. 154(b) by 139 days.

(21) Appl. No.: 15/515,665

(22) PCT Filed: Oct. 2, 2015

(86) PCT No.: PCT/US2015/053710
§ 371 (c)(1),
(2) Date: Mar. 30, 2017

(87) PCT Pub. No.: WO2016/054502
PCT Pub. Date: Apr. 7, 2016

(65) Prior Publication Data
US 2017/0326357 A1    Nov. 16, 2017

Related U.S. Application Data

(60) Provisional application No. 62/059,336, filed on Oct. 3, 2014.

(51) Int. Cl.
*A61N 1/05* (2006.01)
*A61N 2/00* (2006.01)
(Continued)

(52) U.S. Cl.
CPC ............. *A61N 1/0534* (2013.01); *A61N 1/40* (2013.01); *A61N 2/006* (2013.01); *A61N 2/02* (2013.01); *A61N 1/36014* (2013.01)

(58) Field of Classification Search
CPC ........ A61N 1/40; A61N 2/02; A61N 1/36014; A61N 2/006; A61N 1/0534
(Continued)

(56) References Cited

U.S. PATENT DOCUMENTS

| 6,213,933 B1 * | 4/2001 | Lin ......................... A61N 2/02 600/13 |
| 2003/0050527 A1 | 3/2003 | Fox et al. |

(Continued)

FOREIGN PATENT DOCUMENTS

WO    2009042863 A1    4/2009

OTHER PUBLICATIONS

International Search Report for corresponding PCT/US2015/053710, dated Dec. 30, 2015, pp. 1-9.

*Primary Examiner* — Navin Natnithithadha
*Assistant Examiner* — Sunita Reddy
(74) *Attorney, Agent, or Firm* — Tarolli, Sundheim, Covell & Tummino LLP

(57) ABSTRACT

An apparatus for providing deep nerve stimulation to a patient includes a housing for supporting deep nerve stimulation coils. The housing includes a wall with an outer surface for being presented toward the patient to apply the stimulation. A primary coil is supported in a primary chamber of the housing adjacent an inner surface of the wall, opposite the outer surface. Ribs are disposed between the primary coil and the inner surface and upon which the primary coil rests. The ribs define channels through which coolant can be directed to cool a bottom surface of the primary coil during use, the bottom surface of the primary coil being closest to the patient side wall. The primary coil is adapted when energized to produce a broad and deeply penetrating magnetic field capable of hitting a target area of the patient. The secondary coil is configured and arranged to, (Continued)

when energized, focus and shape the field produced by the primary coil so that we can maximize the field strength at the target deep nerve, while minimizing the field at near off-target sensitive areas.

19 Claims, 13 Drawing Sheets

(51) Int. Cl.
 *A61N 1/40* (2006.01)
 *A61N 2/02* (2006.01)
 *A61N 1/36* (2006.01)
(58) Field of Classification Search
 USPC ........................................................ 600/9–15
 See application file for complete search history.

(56) References Cited

U.S. PATENT DOCUMENTS

| | | | |
|---|---|---|---|
| 2004/0263305 A1 | 12/2004 | Oughton, Jr. et al. | |
| 2006/0264692 A1* | 11/2006 | Riehl | A61N 2/006 600/13 |
| 2007/0027411 A1* | 2/2007 | Ella | A61H 7/008 601/7 |
| 2007/0255085 A1 | 11/2007 | Kishawi et al. | |
| 2008/0114199 A1* | 5/2008 | Riehl | A61N 2/006 600/13 |
| 2008/0177128 A1* | 7/2008 | Riehl | A61N 2/006 600/13 |
| 2008/0224808 A1* | 9/2008 | Ghiron | A61N 2/006 335/300 |
| 2009/0287035 A1* | 11/2009 | Dietrich | A61N 1/36017 600/9 |
| 2010/0179455 A1* | 7/2010 | Nebrigic | A61B 18/18 601/15 |
| 2010/0331602 A1 | 12/2010 | Mishelevich et al. | |
| 2011/0046432 A1* | 2/2011 | Simon | A61H 23/00 600/14 |
| 2011/0077452 A1* | 3/2011 | Kolt | A61N 2/02 600/13 |
| 2011/0128105 A1 | 6/2011 | Sevakivi et al. | |
| 2012/0289757 A1* | 11/2012 | Boyden | A61N 5/025 600/1 |
| 2013/0238050 A1* | 9/2013 | Simon | A61N 1/40 607/42 |
| 2013/0245711 A1* | 9/2013 | Simon | A61N 1/3601 607/42 |
| 2013/0317281 A1* | 11/2013 | Schneider | A61N 2/008 600/13 |
| 2014/0200388 A1* | 7/2014 | Schneider | A61N 2/02 600/15 |
| 2014/0257438 A1* | 9/2014 | Simon | A61N 1/0456 607/72 |

* cited by examiner

DEEP NERVE STIMULATOR

CROSS-REFERENCE TO RELATED APPLICATIONS

This application is a 35 U.S.C. 371 National Phase filing of PCT/US2015/053710, filed Oct. 2, 2015, which claims priority from U.S. Provisional Patent Application Ser. No. 62/059,336, filed Oct. 3, 2014, the subject matter of which is incorporated herein by reference in its entirety.

TECHNICAL FIELD

The present disclosure relates to deep nerve stimulation. More specifically, the present disclosure is directed to a deep nerve stimulator with a coil design for producing an asymmetric field for deep nerve stimulation and with advanced cooling features.

BACKGROUND

Magnetic coils are used to apply non-invasive electromagnetic deep nerve stimulation therapy. The stimulation therapy is applied using a magnetic coil constructed of electrically conducting material, such as copper wire, copper tubing, or Litz wire. Typically, these coils can have an inductance in the range of a few μH up to 20 μH, and may or may not be cooled to avoid overheating. The coils are excited with time varying current pulses, in the form of single pulses, pulse trains or other periodic waveforms, in order to produce a corresponding time-varying magnetic field that penetrates the biological tissues. The magnetic field induces an electrical field in the tissues, which is shaped by the electrical conductivities of different tissues and anatomical structures and reaches the nerves buried deep within those structures.

The induced electrical field acting on deep nerve neurons can cause depolarization of the membrane potential of the neuron. If this depolarization reaches a threshold level, the neuron will fire an action potential, or impulse. Whether an electric field stimulates a nerve to a degree sufficient to trigger an action potential depends on a variety of parameters, such as the strength, gradient, duration, and direction of the electric field at the target nerve, as well as the anatomy of the nerve itself. While the nerve anatomy is fixed and cannot be controlled the electric field acting on the nerve can be manipulated.

The general term "field" can refer to either or both of a magnetic field and an electric field, whichever is applicable. Generally speaking, in terms of neural stimulation, the field that produces the stimulus is the electric field acting on the neural structure. Traditionally, to focus an electric field on a specific target, such as in the field of Transcranial Magnetic Stimulation (TMS), a double coil, normally referred to as a figure eight coil or a butterfly coil is used, where the maximum electric field falls along a perpendicular axis from the meeting point of two equal diameter coils.

In order to stimulate deeper targets, one simple solution is to increase the diameter of the two coils. However, increasing the diameter of the coils has the effect of reducing the coil focality. While there have been many attempts to overcome this depth-focality trade-off, the consensus in the field has been that, for traditional coil designs, the ability to stimulate deeper targets is obtained at the expense of a reduction in the coil focality. As a consequence, target depths greater than 4 cm have been considered to be unsafe for the purposes of brain stimulation.

Non-invasive magnetic stimulation of nerve structures deep in the head has received a great deal of attention in the neurological sciences. However, attempts to stimulate structures deep in the brain do so with the intent being to produce a narrow, needle-like field distribution so as to avoid the off-target neural structures or regions ("off-targets") while stimulating the target neural structures or regions ("targets").

Additionally, generating these electric fields can create a great deal of heat that, owing to the fact that the stimulator necessarily is placed in close vicinity to the patient, creates a need for effective cooling. Deep nerve stimulators can be high voltage devices (e.g., 2000 volts) and can generate large electric fields for extended durations. For example, a deep nerve stimulator can be asked to deliver 300 millisecond, 2 Tesla pulses for 5 minutes. Absent effective cooling, coils delivering this level of stimulation could reach skin burn temperature of 42 degrees C. in 10 seconds and could fail due to overheating in 25 seconds.

SUMMARY

The present invention relates to deep nerve stimulation in which electromagnetic coils are designed to produce a magnetic field that induces an electric current in excitable tissue. According to one aspect, an asymmetric magnetic field is used to stimulate deep nerve targets without stimulating near, off-target nerves and other neurological or anatomical structures. In one implementation, nerves located deep within the skull, but outside the brain, can be on-target and, consequentially, the entire brain can be considered off-target. The asymmetric field can be positioned and oriented to stimulate target regions including the nerves while minimizing exposure of the off-target regions distributed around the target region. For example, the asymmetric field can be positioned and oriented to stimulate the facial nerve without stimulating the temporal lobe of the brain.

To achieve this, the stimulation coil of the present invention includes a plurality of sub-coils (i.e., two or more) that are configured and arranged in a predetermined manner to generate an asymmetric magnetic field when the coils are excited. The asymmetric field can be applied to the patient in order to induce an asymmetric electric field in excitable target physiological structures in the patient. This asymmetric field maximizes stimulation of the on-target region and minimizes stimulation of the off-target regions. Since the off-target regions can be distributed asymmetrically around the target, e.g., to one side of the target, a sharply focused field may not be an absolute requirement to effectively stimulate the target while minimizing exposure of the off-target areas. Because of this, the sub-coils can be shaped, sized, positioned, and oriented to modify the shape and form of electric field induced in the anatomical structures so that it can "work around" the off-target regions of these structures while at the same time act on, and apply stimulation therapy to, the on-target regions.

According to one aspect, the plurality of sub-coils can be connected in series and driven from the same stimulus generator running at a fixed power. The electromagnetic fields produced by the individual coils act in concert and mutually affect each other. Thus, in this configuration, each sub-coil contributes to the size, shape, position, orientation, and magnitude of the on-target field. For example, the sub-coils can be configured and arranged to create an asymmetrical field that is broad on one side, allowing for deep penetration to on-target structures, and narrowed or otherwise shaped on other sides to limit the field strength at off-target structures.

For instance, in one implementation, the sub-coils can be circular coils, each having a different radius. The coils can be positioned in close proximity to each other or partially overlapped. By providing coils of different radii and adjusting their relative positions, the shape of the resulting field can be varied. In this simple, two circular coil configuration, the shape of the resulting field can have, for example, a skewed figure-8 shape or a skewed circular shape. In this configuration, it can be desirable to limit the difference between the radii of the coils in order to maintain a relatively focal electric field.

In addition to the relative sizing of the coil radii, the degree of separation or overlap between the coils can be varied. For example, in another implementation, the shape of the induced electric field can be tuned to suit the application by adjusting the degree of separation or overlap between the coils. In another, more complex implementation, in addition to the separation and overlap, the relative orientations of the coils can be adjusted from lying co-planar or in parallel planes to lie in planes that are skewed relative to each other. The number of turns in each coil can also be adjusted.

The degree of shaping necessary can be at least somewhat determined by the specific procedure and the particular physiological structures encountered during that procedure. For example, when stimulating the facial nerve at the geniculate ganglion, it is important to minimize stimulation of the nearby temporal lobe of the brain. Thus, for this application, the coil configuration must be tuned to shape the electric field so that a broad portion of the field can penetrate to the geniculate ganglion while a shaped or narrowed portion of the field avoids, wraps, or bends around the temporal lobe.

There can be a tradeoff between the degree of field shaping and the relative strength of the different portions of the shaped field. As the field is increasingly shaped or distorted, the relative strengths of the shaped portions of the field can be diminished. Thus, for example, a large overlap between coils can provide a great degree of shaping at the expense of on-target field strength, whereas a small overlap or spacing between the coils can provide a lesser degree of shaping with increased on-target field strength. Therefore, it is advantageous to select a coil configuration that presents a compromise between these extremes in order to best fit the shape and strength of the field to the procedure that is being performed.

According to one aspect, the invention relates to an apparatus for providing deep nerve stimulation to a patient includes a housing for supporting deep nerve stimulation coils. The housing includes a wall with an outer surface for being presented toward the patient to apply the stimulation. A primary coil is supported in a primary chamber of the housing adjacent an inner surface of the wall, opposite the outer surface. Ribs are disposed between the primary coil and the inner surface and upon which the primary coil rests. The ribs define channels through which coolant can be directed to cool a bottom surface of the primary coil during use. The bottom surface of the primary coil is closest to the inside, or patient side wall.

According to another aspect, alone or in combination with any other aspects, the housing can include a hub around which the primary coil is wound. The hub defines a central conduit through which coolant flows and is distributed to the channels to cool the primary coil.

According to another aspect, alone or in combination with any other aspects, the hub has a terminal end positioned on the ribs so as to space the terminal end away from the inner surface of the wall at locations between the ribs. The terminal end and the ribs define apertures through which the coolant is directed into the channels from the conduit.

According to another aspect, alone or in combination with any other aspects, the ribs can extend radially from the hub, thereby giving the channels a radial configuration. The coolant can flow from the hub radially outward over the primary coil.

According to another aspect, alone or in combination with any other aspects, the housing can include an outer wall with a curved profile that directs the radially flowing coolant over the opposite surface of the primary coil.

According to another aspect, alone or in combination with any other aspects, the apparatus can include coil clamps that connect with the housing to help maintain the position of the primary coil within the housing. The coil clamps can extend radially from the hub to the outer wall and define therebetween channels into which coolant directed from the outer wall flows radially over a top surface of the primary coil.

According to another aspect, alone or in combination with any other aspects, the housing can include a fluid collecting chamber for collecting coolant after it has flowed over the primary coil. The housing can also include a bubble trap for collecting air bubbles that may form in the coolant during use.

According to another aspect, alone or in combination with any other aspects, the apparatus can include a secondary coil that shapes the electric field generated by the primary coil. The secondary coil can be disposed in a secondary chamber of the housing and at least partially overlying the top surface of the primary coil.

According to another aspect, the invention relates to an apparatus for providing deep nerve stimulation to a target area of a patient. The apparatus includes a housing and a primary coil supported the housing. The primary coil is adapted when energized to produce a broad and deeply penetrating electric field capable of hitting the target area. The apparatus also includes a secondary coil supported in the housing, the secondary coil is configured and arranged to, when energized, shape the field produced by the primary coil.

According to another aspect, alone or in combination with any other aspects, the secondary coil can be configured and arranged to shape the field produced by the primary coil in the direction of an off-target area.

According to another aspect, alone or in combination with any other aspects, the secondary coil can be configured and arranged so that a portion of the secondary coil overlaps a portion of the primary coil.

According to another aspect, alone or in combination with any other aspects, the overlap between the primary and secondary coils can be adjustable so as to tailor the shaping effect that the secondary coil has on the field produced by the primary coil.

According to another aspect, alone or in combination with any other aspects, the primary coil and secondary coil can be wound in series.

According to another aspect, alone or in combination with any other aspects, the primary coil and secondary coil can be wound in opposite directions.

According to another aspect, alone or in combination with any other aspects, the apparatus can include multiple secondary coils for shaping the field produced by the primary coil. The secondary coils can be arranged relative to each other and to the primary coil in a manner selected to shape the field produced by the primary coil.

According to another aspect, the invention relates to a method for providing deep nerve stimulation to a target area of a patient. The method includes utilizing a primary coil to produce, when energized, a broad and deeply penetrating electric field capable of hitting the target area. The method also includes positioning a secondary coil relative to the primary coil in order to when energized shape the field produced by the primary coil.

According to another aspect, alone or in combination with any other aspects, the method can include positioning the secondary coil to shape the field produced by the primary coil in the direction of an off-target area.

According to another aspect, alone or in combination with any other aspects, the method can include positioning the secondary coil to overlap a portion of the primary coil.

According to another aspect, alone or in combination with any other aspects, the method can include adjusting the overlap between the primary and secondary coils to tailor the shaping effect that the secondary coil has on the field produced by the primary coil.

According to another aspect, alone or in combination with any other aspects, the method can include positioning multiple secondary coils relative to the primary coil in order to shape the field produced by the primary coil.

BRIEF DESCRIPTION OF THE DRAWINGS

The present invention is illustrated by way of example and not limitation in the figures of the accompanying drawings, in which like references indicate similar elements and in which.

DESCRIPTION

Figure 1:
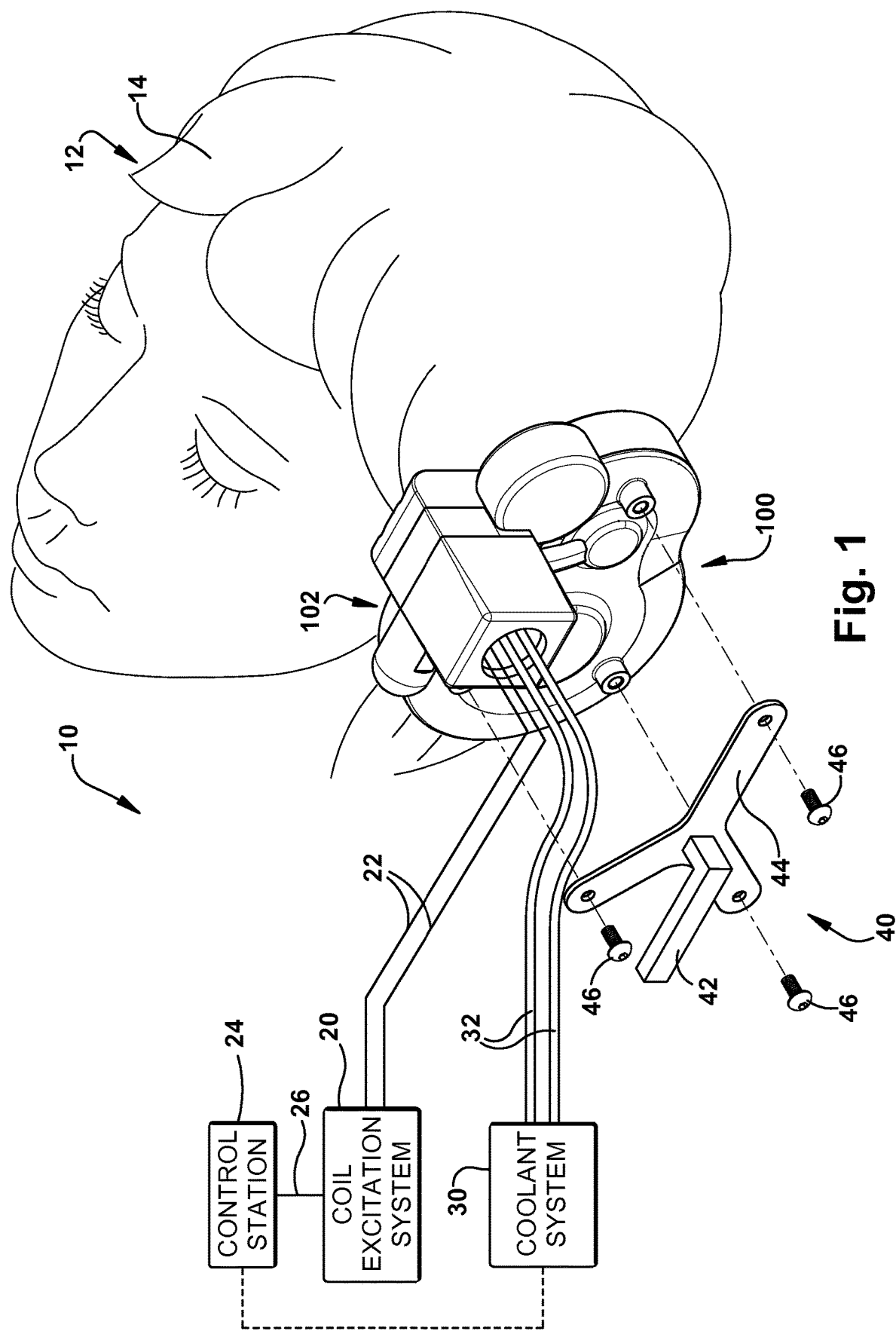
FIG. 1 is a schematic illustration of a system for producing an asymmetric field for deep nerve stimulation, according to the invention.
Figure 2:
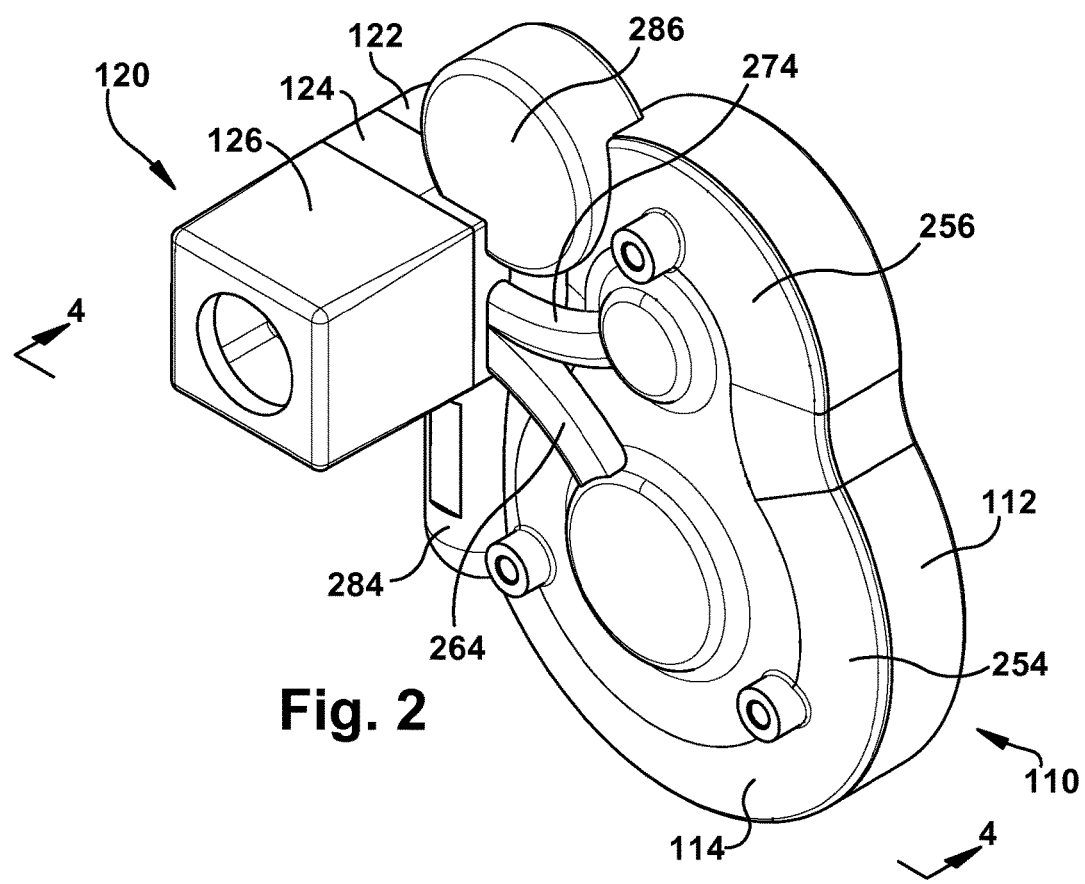
FIG. 2 is a perspective front view illustrating an apparatus that makes up a portion of the system of FIG. 2.
Figure 3:
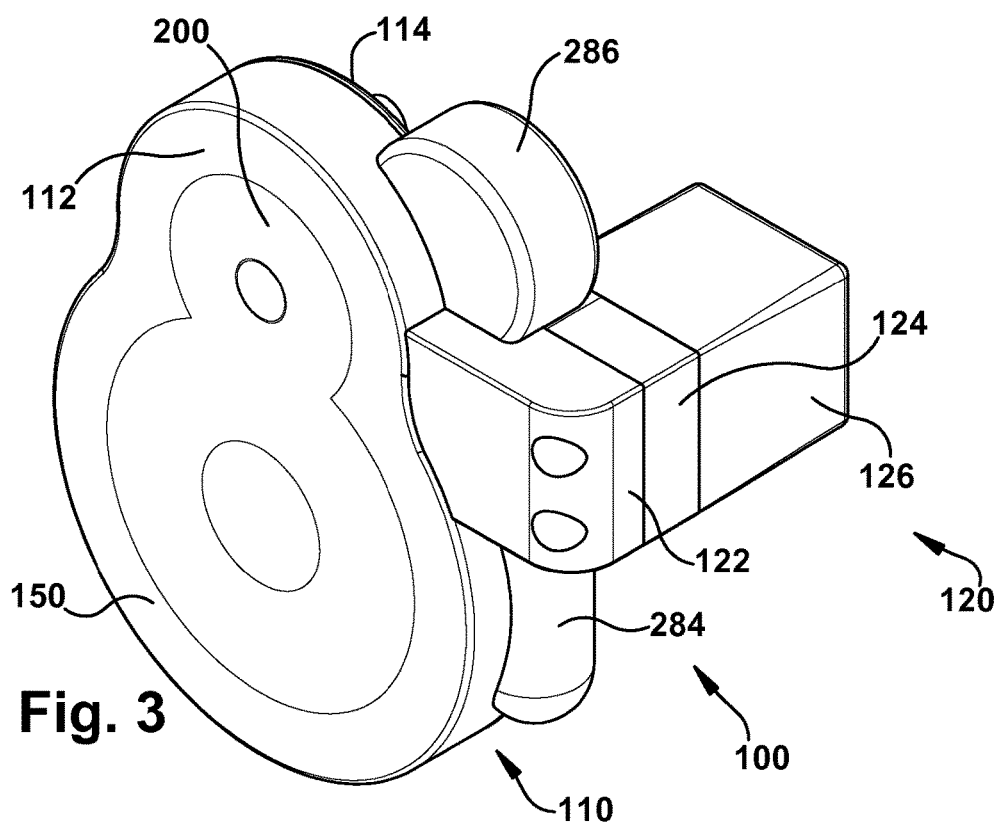
FIG. 3 is a perspective rear view illustrating an apparatus that makes up a portion of the system of FIG. 2.

Referring to FIG. 1, a system 10 for producing an asymmetric field for patient stimulation includes a stimulator 100 for being positioned adjacent or near a patient 12 in order to stimulate one or more physiological structures of the patient. In the arrangement of the embodiment illustrated in FIG. 1, the stimulator 100 can be positioned with a therapy application surface 102 adjacent the patient's head 14 in order to stimulate neurological structures of the patient. In this arrangement, the stimulator 100 can serve as a deep nerve stimulator, a deep brain stimulator, or a combination of both a deep nerve and deep brain stimulator. The stimulator 100 can, however, be positioned adjacent or near any other portion of the patient 12 in order to apply stimulation therapy to other physiological structures.

The stimulator 100 includes at least two coils, concealed within its housing, that are excitable via electric current to generate an electromagnetic field that acts on target physiological structures of the patient 12 to induce in those structures an electric field that stimulates the structures. While not shown in FIG. 1, the coils coincide with the circular lobes of the illustrated stimulator 100. Thus, in the example embodiment illustrated in the figures, the stimulator 100 includes two coils.

Referring to FIG. 1, the system 10 includes a coil excitation system 20, such as an electrical signal generator, that is operatively connected to the stimulator 100, via cables or wires 22. The cables/wires 22 enter the stimulator 100 and are electrically connected to the coils housed therein. The excitation system 20 is operatively connected to a control station 24, such as a computer, that is operative to control, program, or otherwise cause the excitation system to provide a stimulation signal to the stimulator 100 to excite the stimulator coils in a desired manner. For example, time varying current pulses, in the form of single pulses, pulse trains, or other periodic waveforms, can be driven through the coils. The control station 24 can be used to tailor characteristics of the excitation signal, such as the duration of the pulse and the frequency, wavelength, amplitude and shape of the pulse waveform, in order to provide the desired stimulation therapy to the patient.

The illustration of the system 10 as shown in FIG. 1 is not meant to limit the configuration of the control station 24 and coil excitation system 20. These components of the system 10 can have any desired configuration suited to apply the desired excitation signals to the stimulator coils. For example, the control station 24 can be a separate component that is connected to the excitation system 20 via a connection 26 that can be wired or wireless, as shown in FIG. 1. The system 10 could, however, be configured such that the control station 24 and the excitation system 20 are combined as a single unit.

The system 10 also includes a coolant system 30 that is operative to provide a cooling fluid or coolant to the stimulator 100. The coolant system 30 is operatively connected to the stimulator 100 via hoses 32 which deliver coolant to the stimulator and return coolant from the stimulator. The configuration of the coolant system is not important, as long as it is capable of circulating coolant through the stimulator 100 at a desired temperature and flow rate. The coolant system 30 thus can have any desired configuration for achieving this purpose. For example, the coolant system 30 can be an open system in which pre-refrigerated coolant is delivered to the stimulator 100 from a supply reservoir and spent/heated coolant is returned from the stimulator to a return reservoir. Alternatively, the coolant system 30 can include a single reservoir from which the coolant is delivered and to which the coolant is returned, along with a heat exchanger, such as a refrigeration unit, that continually cools the coolant in the reservoir.

The system 10 can utilize a variety of coolants. For example, the system 10 can utilize a silicone oil coolant, which can provide several benefits. Silicone oil can exhibit a comparatively high degree of thermal conductivity per unit mass. Silicone oil can also has dielectric properties that allow it to act as an insulator that prevents arcing from coil to coil, from coil to surrounding structure, and from coil to patient. Alternative coolants could, however, be used.

The system 10 can further include a mounting system 40 for supporting the stimulator 100. The mounting system 40 can, for example, include a base or frame 42 that supports a bracket 44 to which the stimulator 100 can be connected by fastening devices 46, such as threaded fasteners. To facilitate this connection, the stimulator 100 can be configured to include portions for receiving the fastening devices 46, such as threaded fasteners. As shown in FIG. 1, the mounting system 40 can be used to position the flat bottom surface of the stimulator adjacent the patient 12. As described in detail below, this flat bottom surface is thin-walled and is configured to position the coils in as close proximity as possible to the target zone on the patient.

Figure 6:
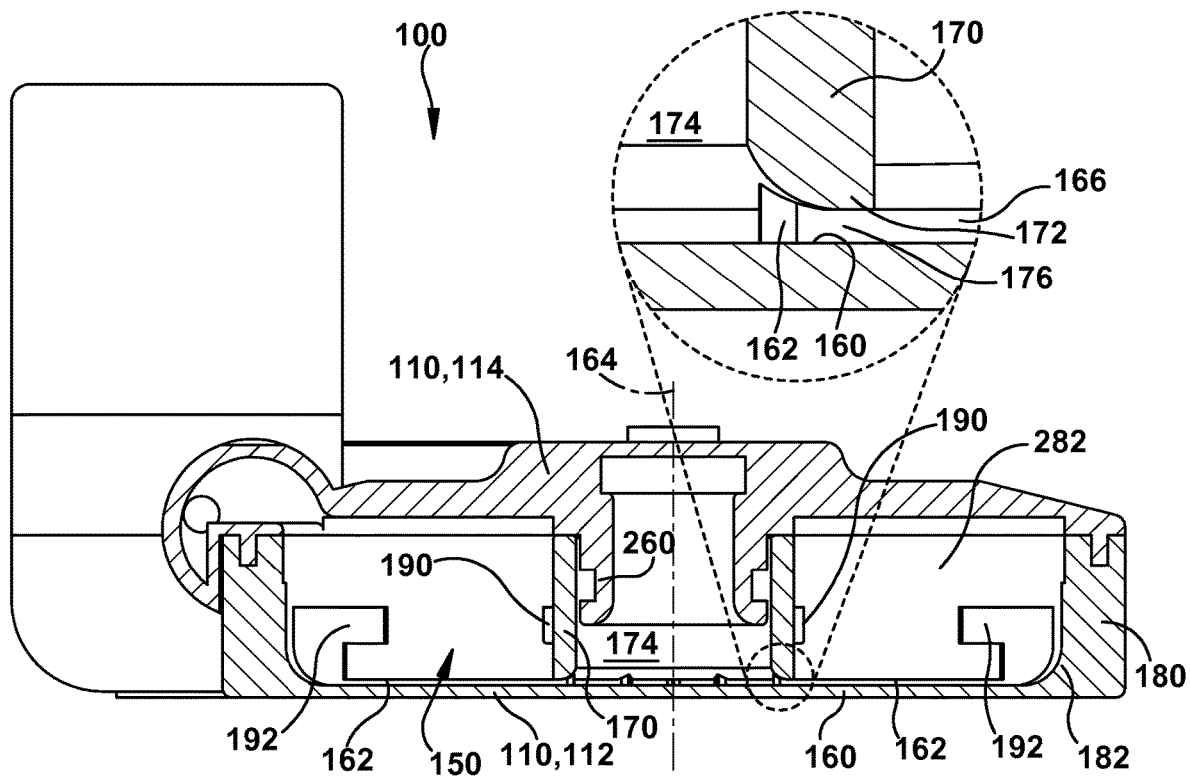
FIG. 6 is a section view generally along line 6-6 in FIG. 4.
Figure 7:
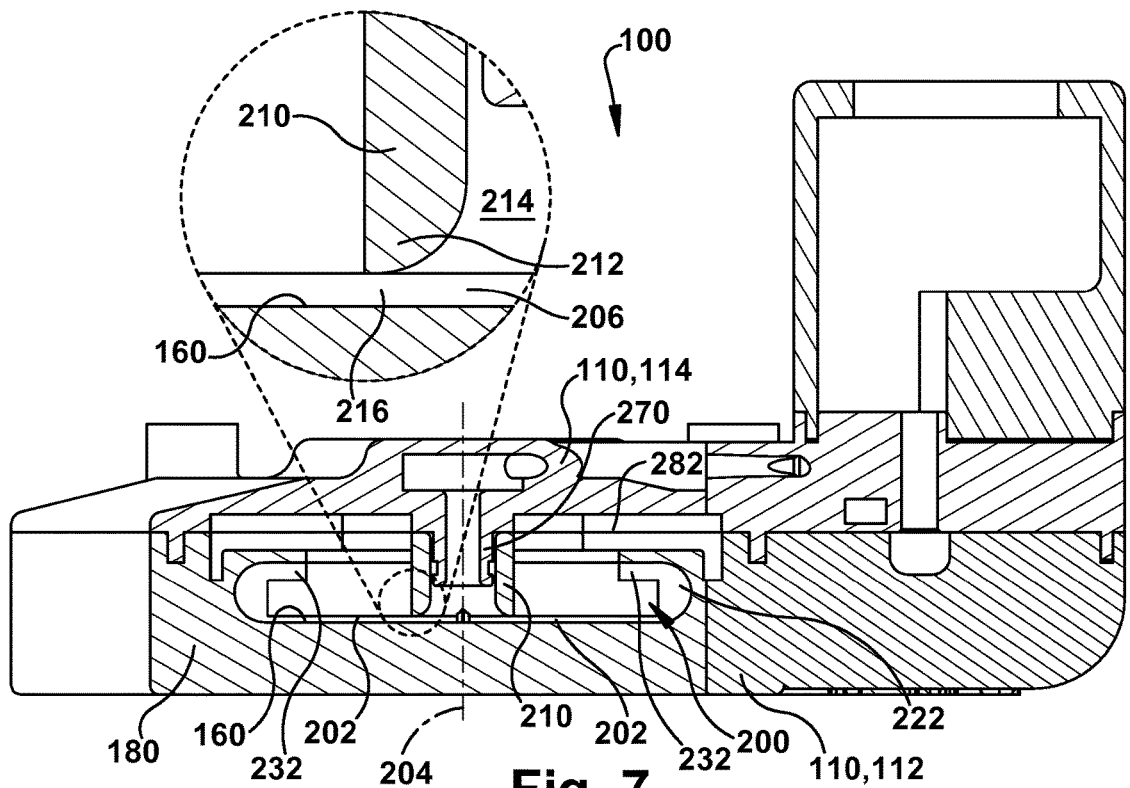
FIG. 7 is a section view generally along line 7-7 in FIG. 4.
Figure 8:
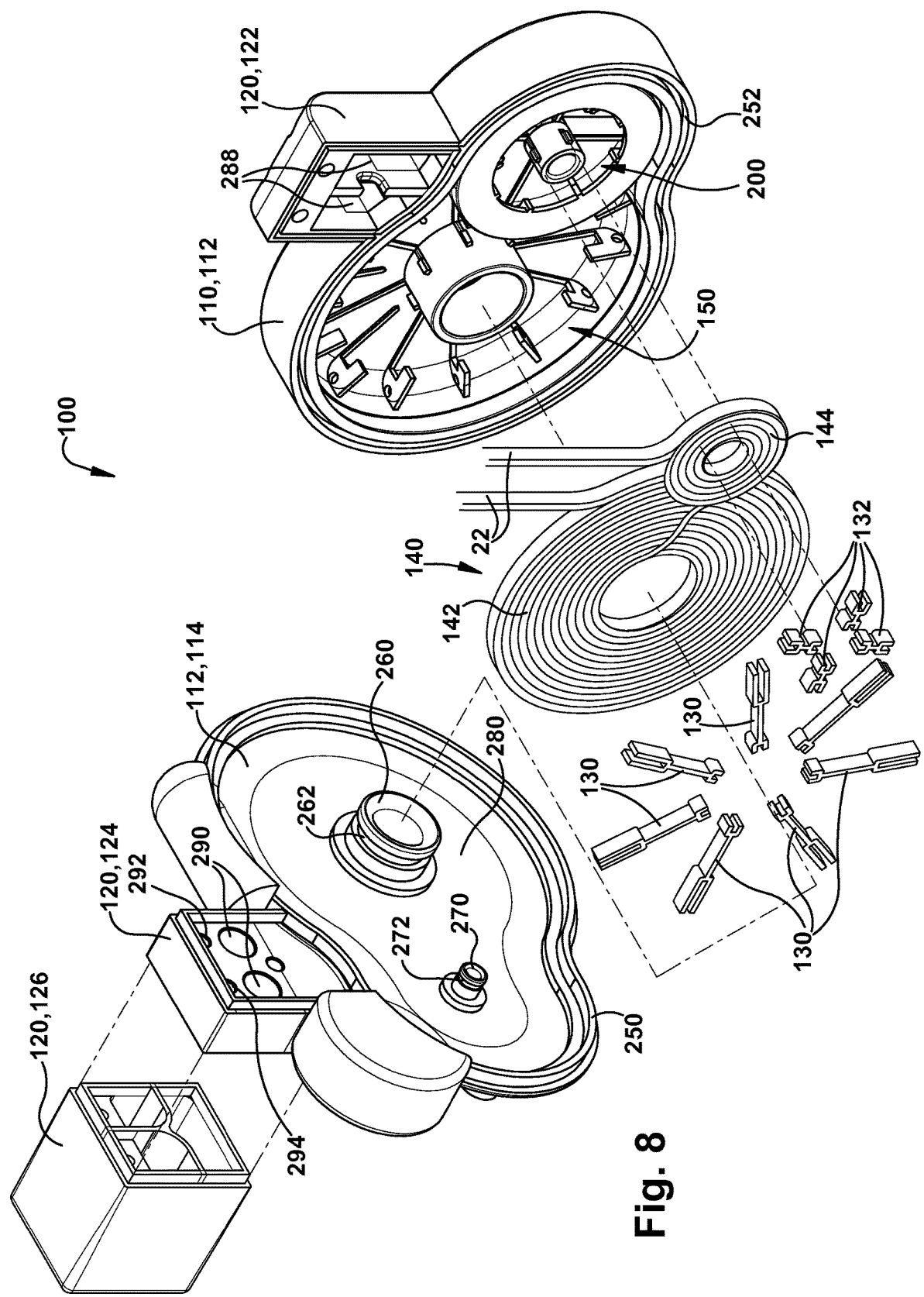
FIG. 8 is an exploded view of the apparatus of FIG. 2.
Figure 9:
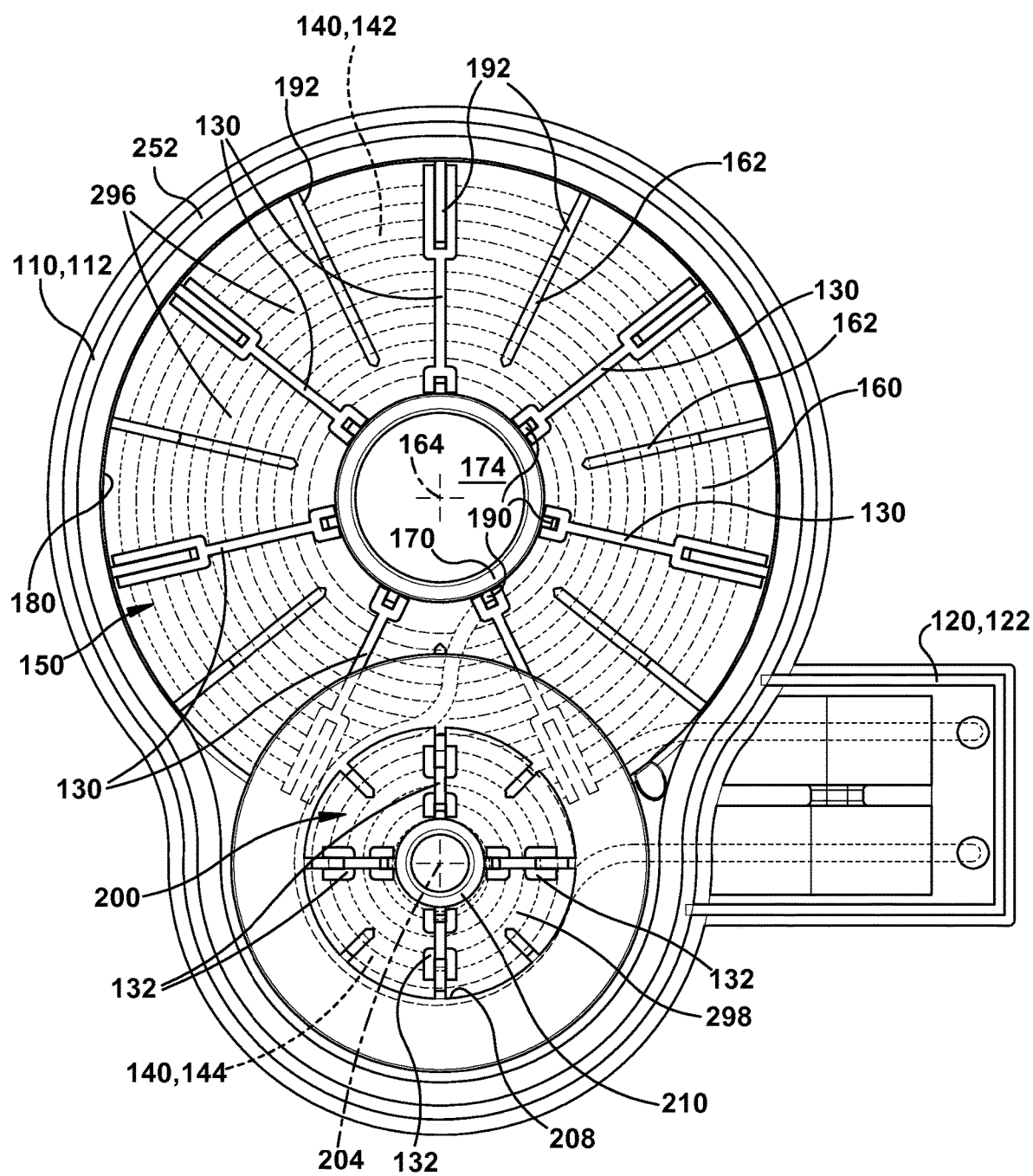
FIG. 9 is a front view of portions of the apparatus of FIG. 2 in a partially assembled condition.

The stimulator 100 is illustrated in greater detail in FIGS. 2-10. Referring generally to FIGS. 2-10, the stimulator 100 includes the following components: a housing 110 including a base 112 and a cover 114, and a junction box 120. Referring to FIG. 8, the stimulator 100 also includes primary coil clamps 130, secondary coil clamps 132, and a coil 140. The coil 140 comprises a single length of conductor material that is wound to form a primary coil 142 and a secondary coil 144.

The coil 140 can be formed from a variety of electrically conductive materials, such as copper wire, copper tubing, or litz wire. The inductance of the coils can be up to 20 µH or more, and can generate a significant amount of heat during some uses. According to one aspect of the invention, the stimulator housing 110 can be adapted to provide cooling features for dissipating some of the heat generated by the coils 140.

The components forming the stimulator 100 can be constructed using a variety of materials and manufacturing processes suited to provide the functional and performance characteristics described herein. The stimulator components can, for example, have plastic or polymer-based constructions, and can include reinforcing materials, such as glass fibers, for added strength. The components can have a single piece construction or a multi-piece construction and can be manufactured using one or more of a variety of processes, such as molding, stamping/pressing, or extrusion. In one particular construction, the components of the stimulator 100 can have a plastic/polymeric construction manufactured using 3D printing techniques. This construction can be advantageous because the 3D printed components can have a one-piece construction and can include recesses and/or voids that cannot be formed in a one-piece construction using some of the more conventional plastic manufacturing methods mentioned above, such as molding.

The stimulator housing base 112 has a lobed configuration including a large, generally cylindrical primary chamber 150 for receiving the primary coil 142 and a smaller, generally cylindrical secondary chamber 200 for receiving the secondary coil 144. In the primary chamber 150, a plurality of ribs 162 project from a bottom wall 160 of the base 112 and extend radially away from a central axis 164 of the primary chamber. The ribs 162 terminate at or near a outer wall of the portion of the housing base 112 that defines primary chamber 150. The primary outer wall extends from the bottom wall 160 and defines the outer periphery and bounds of the primary chamber 150.

A primary hub 170 is positioned in the primary chamber 150 and is centered on the axis 164. The primary hub 170 comprises a cylindrical wall that has a terminal end 172 (see FIG. 6) that is spaced from the bottom wall 160 and is connected to the bottom wall via its being connected to the ribs 162. The primary hub 172 thus, in a sense, "rests" on the hubs although, in the one piece (e.g., 3D printed) construction, the primary hub and the ribs 162 are formed as a single contiguous piece of material.

The cylindrical wall of the primary hub 170 defines a conduit 174 that extends through the hub along the axis 164. The ribs 162 define cooling channels 166 that extend radially away from the primary hub 170 between the ribs. Apertures 176 provide fluid communication between the conduit 174 and the channels 166. The apertures 176 are generally narrow and rectangular, defined by the space between the bottom wall 160 and the terminal end 172 of the primary hub 170. The apertures 176 are bounded on opposite ends by the ribs 162. Through this configuration, there exists a fluid path through the hub 170 toward the bottom wall 160 via the conduit 174, through the apertures 176, and along the bottom wall via the channels 166.

As shown best in FIG. 6, in the area of the primary chamber 150, the outer wall has a generally thick-walled construction. This allows for a peripheral channel 182 with a curved cross-section to be recessed into the outer wall. The curvature of the peripheral channel 182 is configured to merge with the bottom wall 160. In this manner, the cooling channels 166 formed along the bottom wall 160 merge with the peripheral channel 182 of the outer wall 180.

Figure 5:
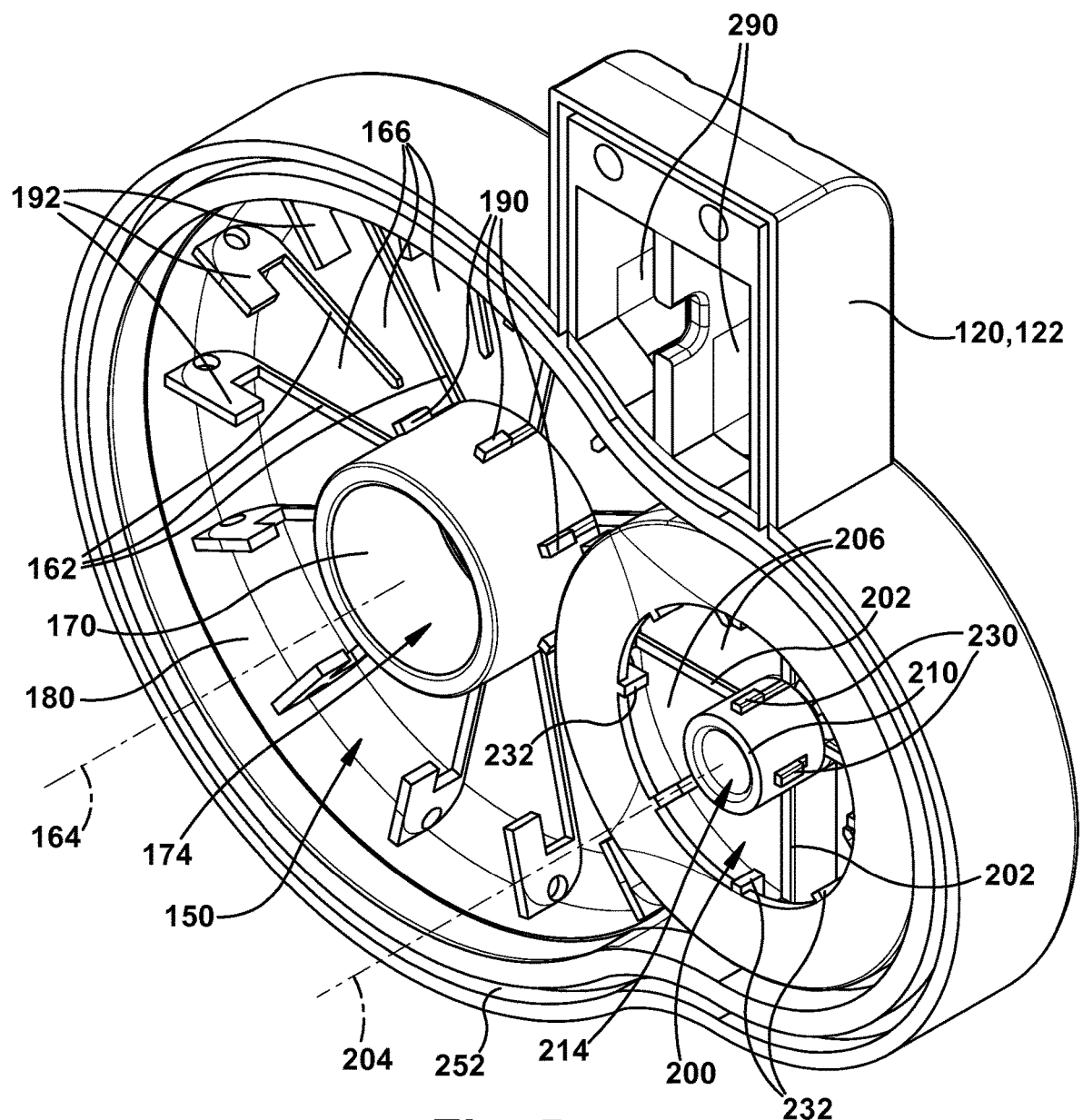
FIG. 5 is a perspective front view of a portion of the apparatus of FIG. 2.

Referring to FIG. 5, the primary hub 170 includes a plurality of coil retention tabs 190 that project radially outward from the cylindrical outer surface of the hub at locations spaced circumferentially about the hub at a predetermined distance above the ribs 162. Coil retention tabs 192 also project radially inward from the outer wall 180 at locations spaced circumferentially along the channel at the same predetermined distance above the ribs 162.

In the secondary chamber 200, a plurality of ribs 202 project from the bottom wall 160 of the base 112 and extend radially away from a central axis 204 of the secondary chamber. The ribs 202 terminate at or near a sidewall 208 of the portion of the housing base 112 that defines secondary chamber 200. The secondary sidewall 208 extends from the bottom wall 160 and defines the outer periphery and bounds of the secondary chamber 200.

A secondary hub 210 is positioned in the secondary chamber 200 and is centered on the axis 204. The secondary hub 210 comprises a cylindrical wall that has a terminal end 212 (see FIG. 7) that is spaced from the bottom wall 160 and is connected to the bottom wall via its being connected to the ribs 202. The secondary hub 210 thus, in a sense, "rests" on the hubs although, in the one piece (e.g., 3D printed) construction, the secondary hub and the ribs 202 are formed as a single contiguous piece of material.

The cylindrical wall of the secondary hub 210 defines a conduit 214 that extends along the axis 204. The ribs 202 define cooling channels 206 that extend radially away from the secondary hub 210 between the ribs. Apertures 216 provide fluid communication between the conduit 214 and the channels 206. The apertures 216 are generally narrow and rectangular, defined by the space between the bottom wall 160 and the terminal end 212 of the secondary hub 210. The apertures 216 are bounded on opposite lateral ends by the ribs 202. Through this configuration, there exists a fluid path through the hub 210 toward the bottom wall 160 via the conduit 214, through the apertures 216, and along the bottom wall via the channels 206.

As shown best in FIG. 7, in the area of the secondary chamber 200, the outer wall 180 has a generally thick-walled construction. This allows for a peripheral channel 222 with a curved cross-section to be recessed into the outer wall 180. The curvature of the peripheral channel 222 is configured to merge with the bottom wall 160. In this manner, the cooling channels 206 formed along the bottom wall 160 merge with the peripheral channel 222 of the outer wall 180.

The secondary hub 210 includes a plurality of coil retention tabs 230 that project radially outward from the cylindrical outer surface of the hub at locations spaced circumferentially about the hub at a predetermined distance above the ribs 202. Coil retention tabs 232 also project radially inward from the outer wall 220 into the peripheral channel 222 at locations spaced circumferentially along the channel at the same predetermined distance above the ribs 202.

Referring especially to FIG. 8, the cover 114 mates with the base 112 to form a liquid tight seal of the housing 110 about its periphery. The connection between the base 112 and cover 114 can be mechanical, e.g., via fasteners, adhesive, e.g., via glue or epoxy, or a combination of these connection methods. A sealant, such as silicone, can also be applied to add to the fluid-tight properties of the housing 110. To facilitate this, the cover 114 can include a projection 250 that extends about periphery and is configured to be received in and mate with a peripheral slot or groove 252 in the base 112. The cover 114 has a lobed construction that generally matches that of the base and includes a primary cover portion 254 for covering the primary chamber 150 and a secondary cover portion 256 for covering the secondary chamber 200. The cover 114 has a domed configuration The cover 114 includes a primary port 260 centrally located on the primary cover portion 254. The primary port 260 is cylindrical and configured to mate with the primary hub 170 when the cover 114 is connected to the base 112. The primary port can include an annular groove 262 for receiving an O-ring for facilitating this connection. The connection between the primary port 260 and the primary hub 170 establishes fluid communication through which cooling fluid can be delivered to the conduit 174 via the primary port.

The cover 114 also includes a secondary port 270 centrally located on the secondary cover portion 256. The secondary port 270 is cylindrical and configured to mate with the secondary hub 210 when the cover 114 is connected to the base 112. The secondary port can include an annular groove 272 for receiving an O-ring for facilitating this connection. The connection between the secondary port 270 and the secondary hub 210 establishes fluid communication through which cooling fluid can be delivered to the conduit 214 via the primary port.

The cover 114 has a recessed or domed inner surface 280 from which the primary and secondary ports 260, 270 extend. When the stimulator is in the assembled condition, the inner surface is spaced from the coils, creating a chamber 282 (See FIGS. 6-7) for collecting cooling fluid after it is circulated around the coils. Connected to this fluid collecting chamber 282 is a primary gas collecting chamber 284, for collecting any air bubbles in the cooling fluid used to cool the primary coil 142, and a primary gas collecting chamber 286, for collecting any air bubbles in the cooling fluid used to cool the secondary coil 144. This helps prevent the formation of air pockets in the area of the coils 142, 144, which can result in areas of intensified heating.

The junction box 120 facilitates both the electrical and cooling fluid connections of the stimulator 100. The junction box 120 includes a base portion 122 formed as a part of the housing base 112, a cover portion 124 formed as a part of the cover 114, and a separate cover 126. The base portion 122 receives and guides the end portions or leads 22 of the coil wires into the junction box 120 and includes portions 288 that serve as conduits for directing those wires out of the stimulator housing 110. Within these portions 288, a sealant, such as silicone, a potting material, or a resin, can be used to prevent cooling fluid from escaping via the cable channels. The cover portion 124 includes apertures 290 through which the coil leads 22 can extend through, into and through the cover 126 to exit the stimulator 100.

Figure 4:
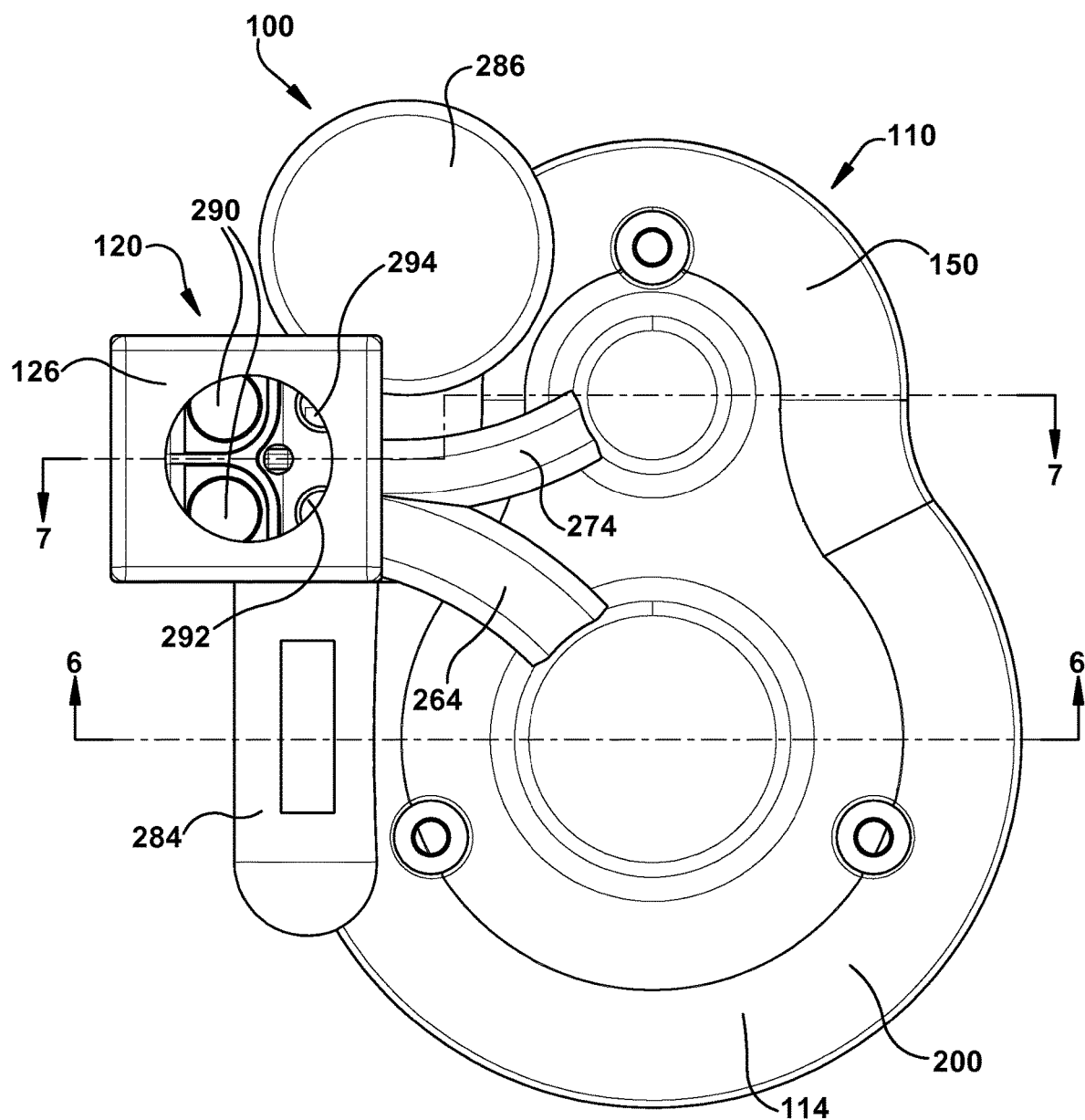
FIG. 4 is a front plan view of the apparatus of FIG. 2.

The cover portion 124 of the junction box 120 handles the inflow and outflow of the cooling fluid and includes a fluid inlet 292 and a fluid outlet 294, each of which is adapted with fluid connection features for facilitating their connection with fluid delivery devices, such as hoses or hose connectors. Referring to FIG. 4, the cover 114 includes a primary channel 264 for delivering cooling fluid from the junction box 120 to the primary port 260 and a secondary channel 274 conduit for delivering cooling fluid from the junction box to the secondary port 270. Both the primary and secondary channels 264, 274 are connected in fluid communication with the cooling fluid inlet 292. The fluid outlet 294 is connected in fluid communication with the gas collection chambers 284, 286, which have openings exposed on the inner surface 280 of the cover 114, thus providing fluid communication between the gas collection chambers and the fluid collection chamber 282 when the stimulator 100 is in the assembled condition.

To assemble the stimulator 100, the coil wire is wrapped around the primary hub 170 to form the primary coil 142 and around the secondary hub 210 to form the secondary coil. The wire leads 22 are fed through the base portion 122 of the junction box and sealed. Next, the primary coil clamps 130 are installed on their respective coil retention tabs 190, 192, and the secondary coil clamps 132 are installed on their respective coil retention tabs 230, 232. The coil clamps 130, 132 define radially extending primary and secondary fluid channels 296, 298 along the coils on the side opposite the channels 166, 206. The cover 114 is assembled with the base 112, and the connections are made with the coil excitation wiring and cooling system tubes/hoses.

Figure 10A:
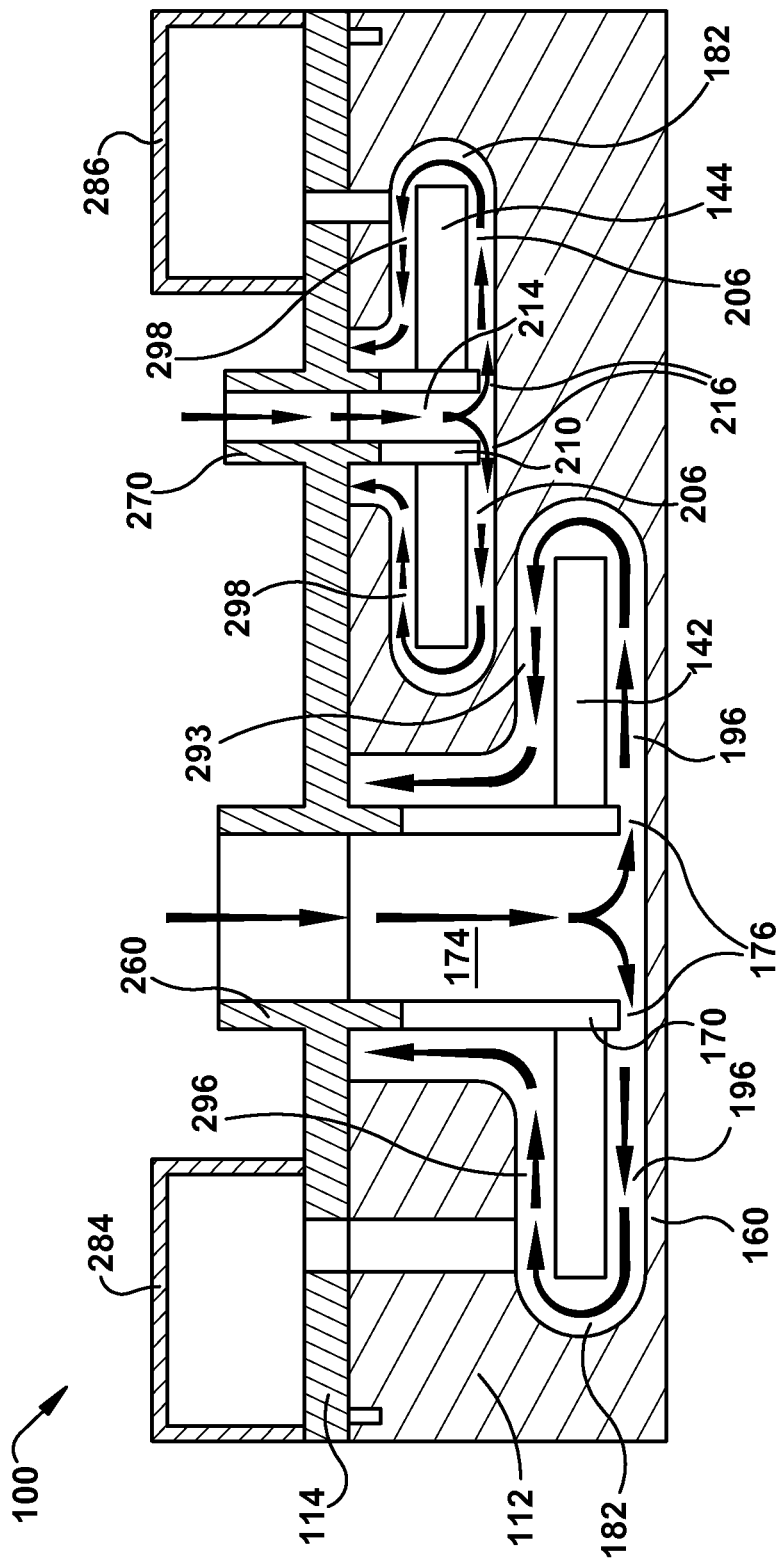
FIGS. 10A-10E are schematic views illustrating the operation of portions of the apparatus of FIG. 2.

In operation, the channeled cooling configuration of the stimulator 100 circulates cooling fluid over the coils 142, 144 to help prevent excessive heating not only of the stimulator as a whole, but also in any localized areas. FIG. 10A illustrates schematically the general direction of flow in the stimulator 100.

On the primary side, cooling fluid is delivered via the primary port 260. The fluid passes through the primary port 260 and enters the fluid conduit 174 defined by the primary hub 170. Adjacent the bottom wall 160, the fluid passes through the apertures 176 and enters the channels 196. The fluid is guided to flow radially outward from the primary hub 170 in the channels 196 and thus flows along and cools the primary coil 142 from its lower side. The fluid is redirected by the curved side wall of the peripheral channel 182 to flow radially inward, guided through the channels 296 defined by the primary coil clamps 130, and thus flows along and cools the primary coil 142 from its upper side. The fluid is directed upward and into the fluid collecting chamber 282 defined by the cover 114. The fluid passes through the fluid collecting chamber 282, enters the junction box 120, and exits via the fluid outlet 294. Any air bubbles present in the fluid collecting chamber 282 on the primary coil side will collect in the primary gas collection chamber 284, due to its being oriented vertically upward, as viewed in FIG. 1, during use.

On the secondary side, cooling fluid is delivered via the secondary port 270. The fluid passes through the secondary port 270 and enters the fluid conduit 214 defined by the secondary hub 210. Adjacent the bottom wall 160, the fluid passes through the apertures 216 and enters the channels 206. The fluid is guided to flow radially outward from the secondary hub 210 in the channels 206 and thus flows along and cools the secondary coil 144 from its lower side. The fluid is redirected by the curved side wall of the peripheral channel 182 to flow radially inward, guided through the channels 298 defined by the secondary coil clamps 132, and thus flows along and cools the secondary coil 144 from its upper side. The fluid is directed upward and into the fluid collecting chamber 282 defined by the cover 114. The fluid passes through the fluid collecting chamber 282, enters the junction box 120, and exits via the fluid outlet 294. Any air bubbles present in the fluid collecting chamber 282 on the secondary coil side will collect in the secondary gas collection chamber 286, due to its being oriented vertically upward, as viewed in FIG. 1, during use.

Figure 10B:
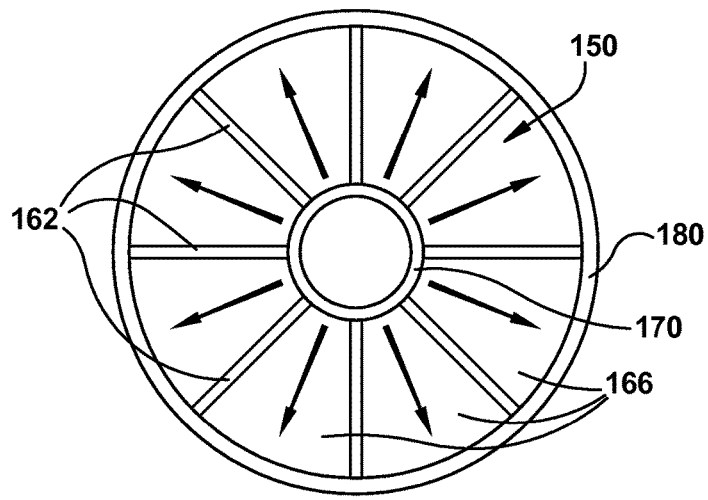

According to the above, referring to FIG. 10B, the coolant flow (shown on the primary side only) is generally radial in nature due to the radial configuration of the channels 166. Coolant is directed from the hub 170 radially over the bottom surface (closest to the patient) of the coils outward toward the periphery of the chamber 150, where it is redirected over the top and circulated as described above. Those skilled in the art will appreciate that flow paths can be altered simply by adjusting the configuration of the ribs 162 and, thereby, the channels 166.

Figure 10C:
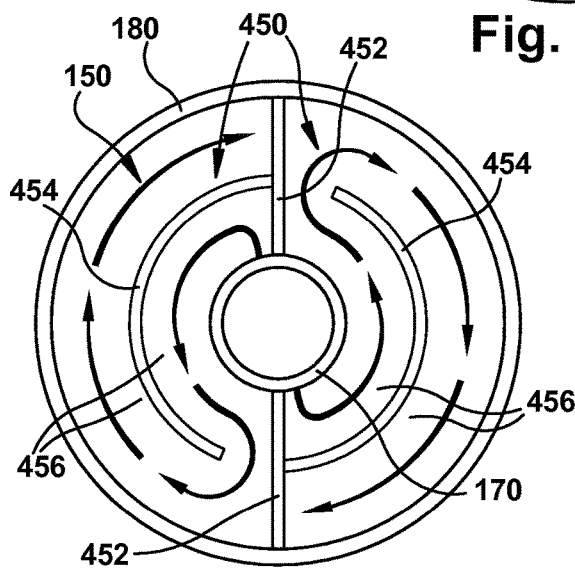

For example, as shown in FIG. 10C, the chamber 150 can be divided into isolated halves or hemispheres 450 by walls 452 that extend from the hub 170 to the outer wall 180. Within each halve 450, curved ribs 454 define a serpentine channel 456 through which the coolant can be directed.

Figure 10D:
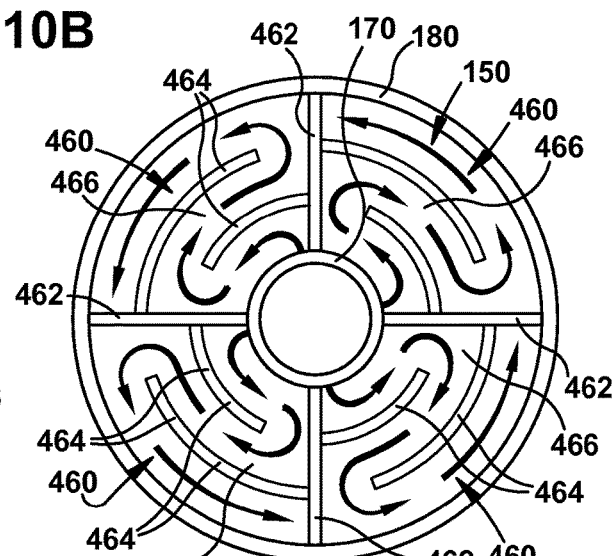

As another example, as shown in FIG. 10D, the chamber 150 can be divided into isolated quadrants 460 by walls 462 that extend from the hub 170 to the outer wall 180. Within each quadrant 460, curved ribs 464 define a serpentine channel 466 through which the coolant can be directed.

Figure 10E:
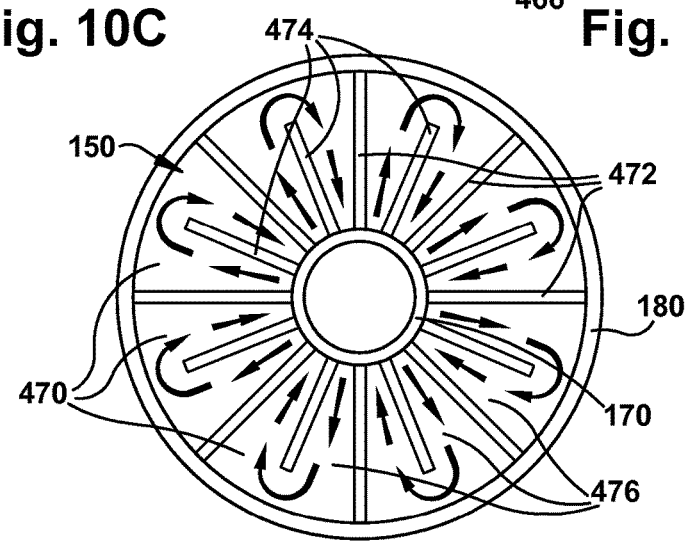

As another example, as shown in FIG. 10E, the chamber 150 can be divided into isolated radial segments 470 by walls 472 that extend from the hub 170 to the outer wall 180. Within each radial segment 470, ribs 474 extend to define a serpentine channel 466 through which the coolant can be directed.

Through circulation as described above, the channeled cooling can help maintain the temperature of the stimulator within desired limits during use. Advantageously, the configuration of the hubs 170, 210 and their respective apertures 176, 216 and radially extending chambers 196, 206 distributes the cooling fluid efficiently and effectively over the coil surfaces, which allows the primary coil 142 to be positioned in close proximity to the bottom wall 160. This allows for the coils to be positioned as close as possible to the patient so that the stronger portions of the magnetic field, i.e., those closer to the coils, can reach the target in the patient.

In the embodiment illustrated in FIGS. 1-10, the stimulator 100 is of a two-coil configuration including a large primary coil 142 and a smaller secondary coil 144. The secondary coil 144 partially overlaps the primary coil 142 and is positioned behind the primary coil when viewed with respect to the therapy applying surface 102 of the stimulator 100. It will be appreciated that the configuration of the components of the stimulator housing 110, especially the base 112 and the cover 114, are configured to cooperate with the specific coil configuration that is shown in FIGS. 1-10. As the coil configuration changes, so does the configuration of the stimulator housing 100. Those skilled in the art, however, will appreciate that the channeled cooling functionality displayed by the illustrated stimulator configuration, and the structures and features implemented in the stimulator design in order to achieve that functionality, can be implemented in stimulator housing configurations designed to house any of the coil configurations described herein.

According to the invention, the coils 142, 144 are wound and positioned in order to produce a field that has a desired shape, typically asymmetric by design, that is conducive to applying deep nerve stimulation therapy to target neural structures or reg10ns ("targets") while avoiding off-target neural structures or regions ("off-targets"). The following configuration characteristics of the primary and secondary coils can be adjusted to achieve this purpose: the size of the coils, the number of windings in the coils, the winding direction of the coils, the relative positions of the coils, and the number of primary and secondary coils. In the embodiments illustrated herein, the coils are series wound coils, i.e., all coils are wound from a single length of wire. In this manner, both the primary and secondary coils contribute to the on-target field. By adjusting these characteristics, the fields generated by the coils field are shaped to the desired asymmetric shape.

By "shaped" or "shaping," it is meant that the secondary coil is configured to produce asymmetry in at least one of the magnitude, direction, and extent of the field produced by the coil 140 as a whole. With this understanding, this shaping is described herein in some respects with regard to how the presence of the secondary coil 144 affects the shape of the field that the primary coil 142 would produce on its own. The shaping effect of the secondary coil 144 on the field of the primary coil 142 is therefore described in terms of curtailing, reducing, restricting, neutralizing, blocking, subtracting, negating, eliminating, counteracting, lessening or otherwise altering one or more of the magnitude, direction, and extent of the field of the primary coil in some respect.

One particular therapy for which the stimulator 100 can be used is the stimulation of the facial nerve system. The term "facial nerve system" as used herein includes, but is not limited to, the facial nerve, the entry region of the facial nerve into the internal auditory canal/internal acoustic meatus, the geniculate ganglion, the tympanic plexus, paratympanic organ(s), the intermediate nerve (of Wrisberg), the pterygopalatine/sphenopalatine nerves and ganglion, the petrosal nerves, the ethmoidal nerves, the palatine nerves, the vidian nerve, the sensory and motor fibers of any of the aforementioned structures, fibers of passage through the aforementioned structures, the communicating branches and connections of the aforementioned structures, and the communicating branches and connections between the aforementioned structures and the ophthalmic, trigeminal, glossopharyngeal, cervical, or vagal nerves. These components of the facial nerve system are in the vicinity of, in proximity to, or are proximate to the ear.

When stimulating the facial nerve system, it has been shown that latent or lasting effects are better realized with longer duration of the applied stimulation. Thus, it can be desirable to apply some stimulation therapies for long durations, such as up to five minutes or longer. The problem, which the present invention addresses, however, is that there are often adjacent off-target structures for which this prolonged exposure is undesirable. For instance, in the example of some of the facial nerve system mentioned above, adjacent off-target structures for which prolonged exposure to stimulation fields include the brain in general and, more specifically, the temporal lobe.

The identity and position of the off-target structures changes, of course, depending on the particular target. And the relative positions of the target and off-target structures is often asymmetrical in nature. By adjusting the coil characteristics identified above, an asymmetric field can be achieved. Coupling this asymmetrically shaped field with the ability to select its position and orientation via placement of the stimulator 100 relative to the patient, the shaped field can stimulate the targets while avoiding the off-targets.

FIGS. 11-16 illustrate the electric fields of various coil configurations, each of which can be constructed in the manner described above with regard to the example embodiment of FIGS. 1-10. To clarify the figures, only the strongest portions of the fields are illustrated. Those skilled in the art will appreciate that the gradients of the fields will diminish based on factors such as distance from the coils and the medium upon which the field acts. Ideally, the strongest portion of the fields, i.e., those illustrated will hit the target completely and miss the off-target structures completely. In reality, however, some off-target stimulation can occur and, also, some stimulation therapy can be applied via a less than optimum strength field. The goal of the invention is to tailor the induced electric field to maximize the on-target coverage, while minimizing any off-target effects.

Figure 11:
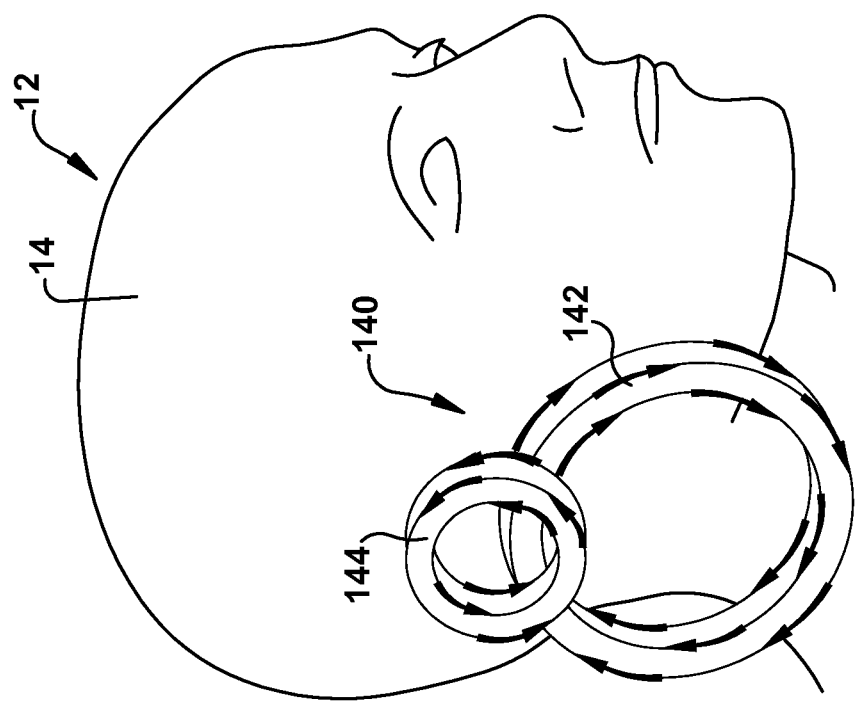
FIG. 11 illustrates schematically the operation of a portion of the apparatus of FIG. 2, according to one example configuration.

FIG. 11 illustrates the position and orientation of the coils 140 relative to the patient 12, particularly the patient's head 14, during use of the stimulator 100 when positioned as shown in FIG. 1. Wired in series, the current in the primary coil 142 flows in a clockwise direction as viewed in FIG. 11, so the electric field generated by this coil is directed or "pushes" into the patient's head 14. Current in the secondary coil 144 flows in a counterclockwise direction, so the electric field generated by this coil is directed or "pushes" away from the patient's head 14. The coil configuration and positioning relative to the patient 12 produces the electric field illustrated in FIG. 12.

Figure 12:
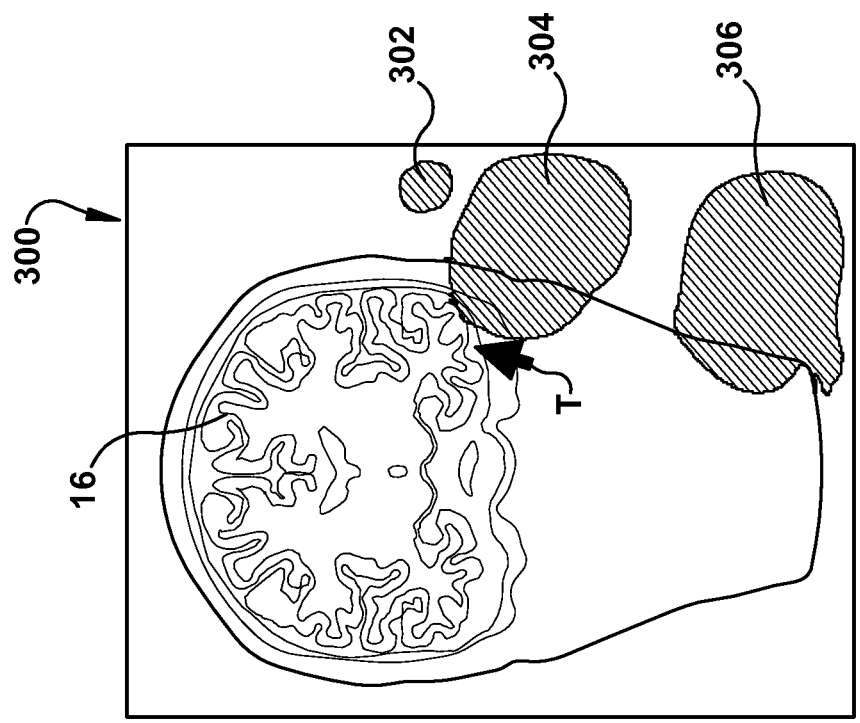
FIG. 12 illustrates the effectiveness of the apparatus configured according to FIG. 11.

Referring to FIG. 12, the electric field 300 generated by the coil arrangement of FIG. 11 is an asymmetrical field that includes an upper field region 302, a middle field region 304, and a lower field region 306. The asymmetrical nature of the electric field 300 is a result of the primary/secondary coil configuration implemented in the stimulator 100. The upper field region 302 is a very small region generated primarily by the small secondary coil 144. The lower field region 316 is a large region generated primarily by the large primary coil 142. The middle field region 304 would have size/shape characteristics similar to the lower field region 302 but for the presence of the secondary coil 144, which helps shape the middle field region.

Acting alone, the primary coil 142 would generate a deep penetrating but broad electric field, whereas the secondary coil 144 would generate a shallow penetrating but focused electric field. By positioning the coils 142, 144 as shown in FIG. 11 and configuring the coils in series and wound in the illustrated opposing directions, the deep penetrating middle field region 304 generated primarily by the primary coil 142 is shaped by the field generated by the secondary coil 144 as shown in FIG. 12. This allows for positioning the stimulator 100 so that the middle field region 304 hits the target T, while the upper field region 302 avoids off-target structures in the brain 16. Advantageously, the lower field region 306 can be used to modulate additional nerves, such as the vagus or glossopharyngeal nerves.

Figure 13:
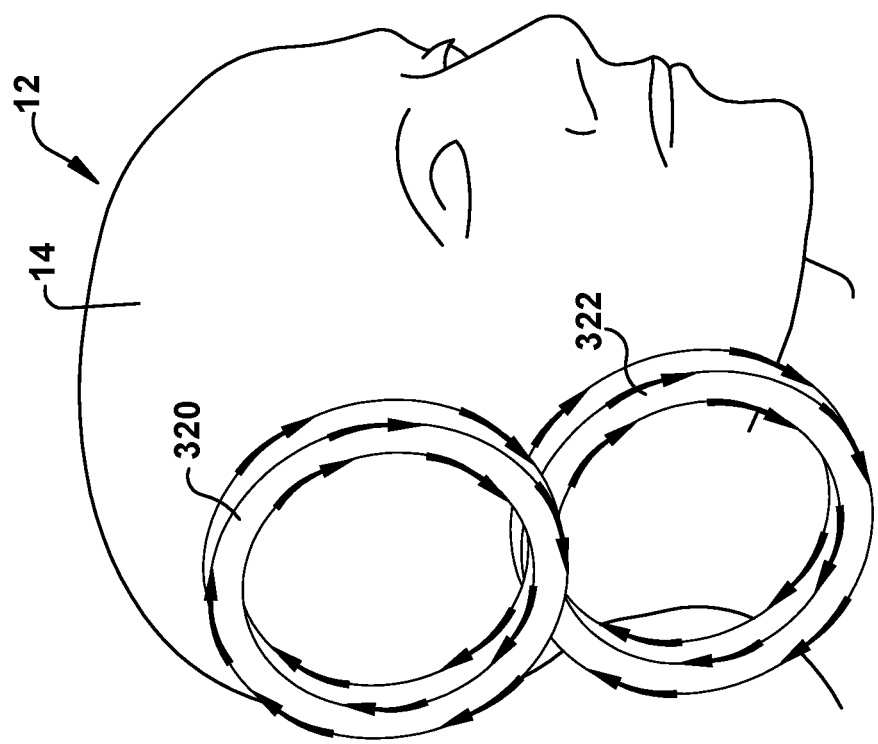
FIG. 13 illustrates schematically the operation of a portion of a conventional apparatus for purposes of comparison.

For the sake of comparison, FIG. 13 illustrates the position and orientation of the coils of a conventional stimulator, which incorporates a conventional figure eight coil configuration. The stimulator includes two coils 320, 322 that are essentially identical and wound in opposite directions. The coils 320, 322 of FIG. 13, positioned relative to the patient 12 as shown, produces the electric field illustrated in FIG. 14.

Figure 14:
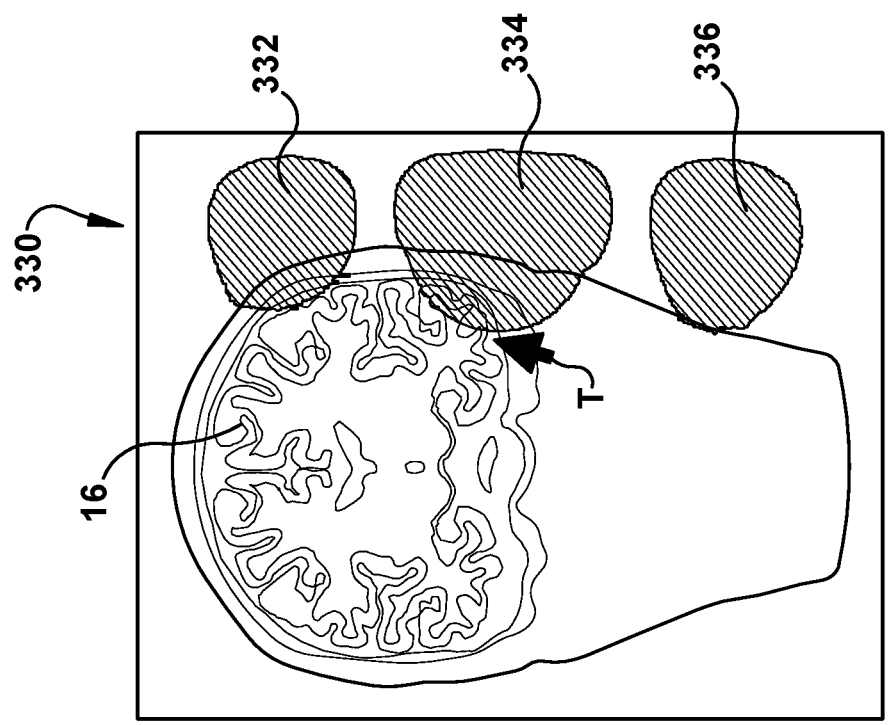
FIG. 14 illustrates the effectiveness of the comparative example of FIG. 13.

Referring to FIG. 14, the stimulator 320 generates an electric field 330 that is symmetrical and includes three regions: an upper field region 332, a middle field region 334, and a lower field region 336. As can be seen in FIG. 14, the middle field region 334 penetrates the deepest into the patient and therefore is the preferred field with which to apply stimulation therapy. The middle field region 334 does not, however, penetrate much deeper than the upper and lower regions 332, 336. As a result, it is clear to see that positioning the middle field region 334 to stimulate the target T results in the upper field 332 hitting the off-target structure of the brain 16.

From this, it can be appreciated that the position of the field 330 relative to the patient's head 14 is limited by the spatial and geometric limitations of the stimulator itself. The stimulator should be maintained close enough to the patient's head to ensure the desired degree of penetration. With these limitations in place, it becomes clear that the figure eight coil stimulator of FIG. 13 is incapable of hitting the target T without also hitting off-target structures.

Referring to FIGS. 11-12, it will also be appreciated that the coil configuration of the stimulator 100 shapes the electric field 300 by shaping it in the upper region 302, which allows the middle region 304 to reach the target while avoiding off-target structures. In this implementation, the stimulator 100 is positioned so that the field 300 reaches the target, e.g., the geniculate ganglion, while avoiding the region of the temporal lobe which is situated just above. A significantly reduced field is generated on the parietal and temporal lobes of the brain by the asymmetrical field 300 at the expense of a small drop in field strength at the target T. This small drop, however, is overcome by the ability to maneuver the stimulator 100 so that the field 300 reaches the target T.

The stimulator 100 is not limited to coil arrays of one large primary and one small secondary coil. Additional small coils can be placed to further shape/curtail the field in the direction of specific off-target areas for which stimulation is not desired. Increasing the number of secondary coils increases the overall inductance of the coil array, with the benefit of an even more specially shaped field. This is illustrated in FIG. 15.

Figure 15:
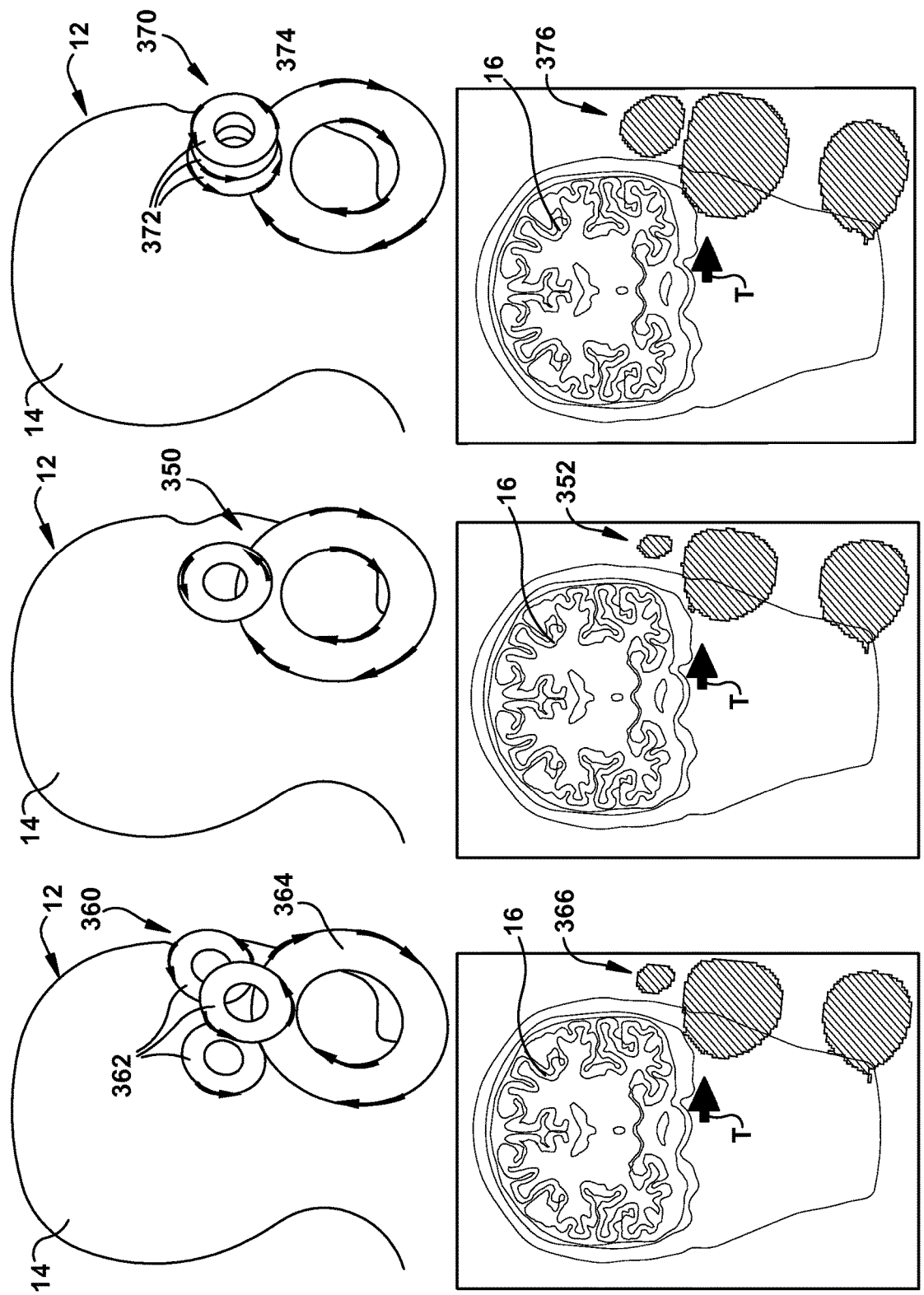
FIG. 15 illustrates schematically the operation of a portion of the apparatus of FIG. 2, according to three more example configurations and also illustrates the effectiveness of those configurations.

FIG. 15 illustrates coil configurations that demonstrate the effects of incorporating multiple secondary coils. For each coil configuration in FIG. 15, the primary coil is the same. Beginning in the middle, coil configuration 350 is similar in nature to the coil configuration of the stimulator 100 of FIGS. 1-10 and is included to compare and contrast with the other coil configurations in FIG. 15. The coil configuration 350 produces the electric field 352.

Coil configuration 360, on the left in FIG. 15, includes three secondary coils 362 that are arranged with two of the coils positioned adjacent to each other at the edge of the circumference of the primary coil 364. The remaining secondary coil 362 is positioned overlying portions of both of the other secondary coils and the primary coil 364. Coil configuration 360 essentially takes the configuration 350 and adds two more secondary coils. As shown in FIG. 15, the resulting field 366 generally maintains the form of the field 352 with increased magnitude due to the additional coils and the corresponding increase in overall inductance of the coils. The increased "push" produced by the additional secondary coils 362 does appear to skew the middle portion of the electric field 366 slightly upward as well. Because hitting target structures and avoiding off-target structures can be a matter of millimeter adjustments or less, the shaping of the field 366 produced by the coil configuration 360 can be beneficial.

Coil configuration 370, on the left in FIG. 15, includes three secondary coils 372 that are arranged concentrically on top of each other overlying the primary coil 374. Coil configuration 370 essentially takes the configuration 350 and adds a second secondary coil on top. As shown in FIG. 15, the resulting field 376 has a significantly increased magnitude due to the additional coil and the corresponding increase in overall inductance of the coils. The increased "push" produced by the additional secondary coil 372 does skew the middle portion of the electric field 376 upward toward the secondary coil. The magnitude of the upper portion of the electric field 376 also increases significantly. Because hitting target structures and avoiding off-target structures can be a matter of millimeter adjustments or less, the shaping of the field 376 produced by the coil configuration 370 can also be beneficial.

Figure 16:
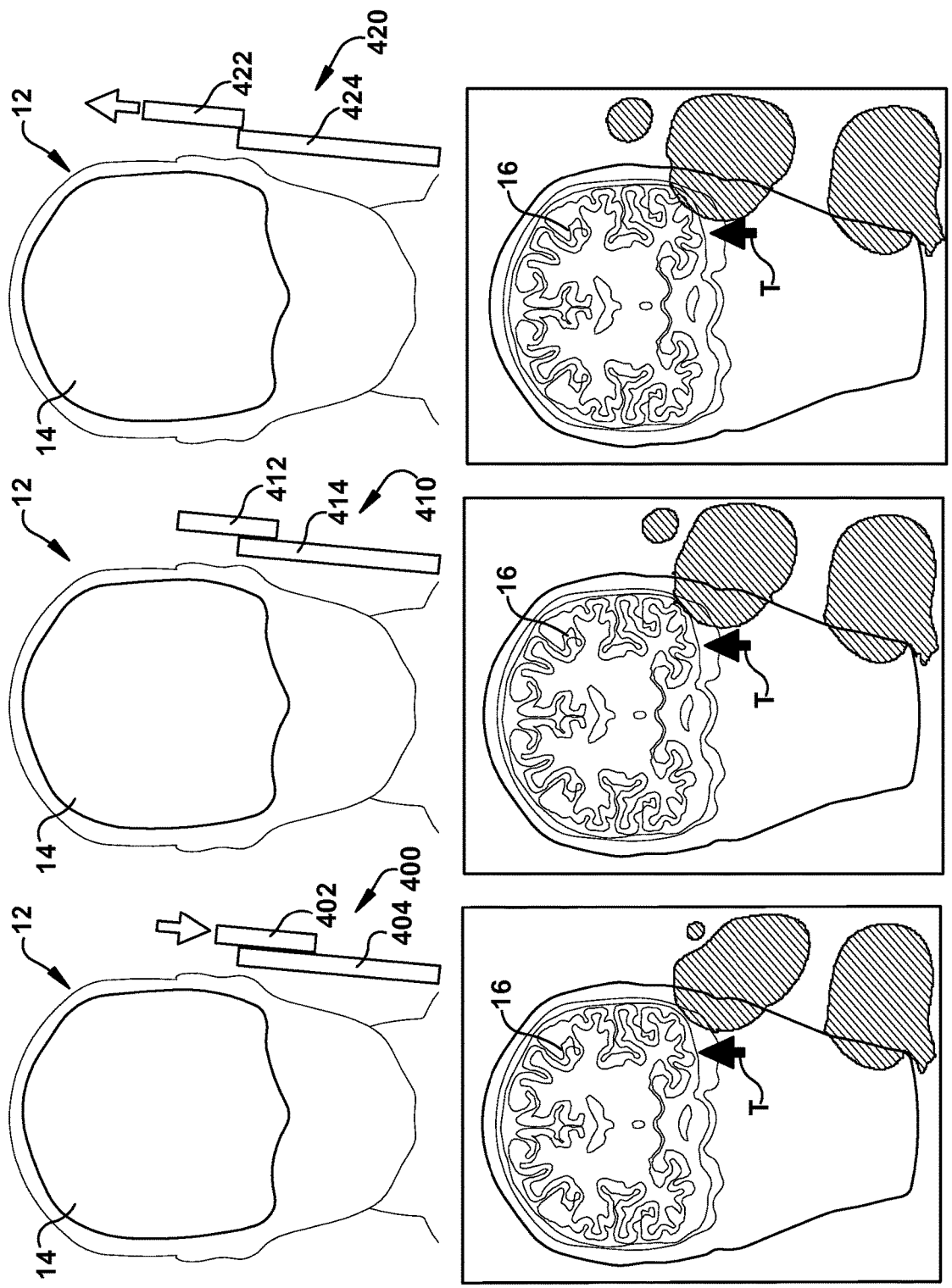
FIG. 16 illustrates schematically the operation of a portion of the apparatus of FIG. 2, according to three more example configurations and also illustrates the effectiveness of those configurations.

The stimulator 100 also is not limited to the coil positions illustrated in FIGS. 1-10. FIG. 16 illustrates three different stimulator configurations in which the primary and secondary coils are arranged in different positions relative to each other. The three different positions illustrated in FIG. 16 show how the position of the secondary coil relative to the primary coil can affect the electric field produced by the stimulator. The primary and secondary coils can, for example, be similar or identical to those implemented in the stimulator 100 illustrated in FIGS. 1-10.

Referring to FIG. 16, at position 1 (left), the coil configuration 400 is configured with a high degree of overlap of the secondary coil 402 over the primary coil 404. In this configuration, almost the entire secondary coil 402 overlaps the primary coil 404. The resulting electric field 406 has a middle region that is highly shaped and is bent or curved upward and inboard of the small upper region of the field.

At position 2 (middle), the coil configuration 410 is configured with a lesser degree of overlap of the secondary coil 412 over the primary coil 414. In this configuration, the center of the secondary coil 412 is aligned approximately with the circumferential edge of the primary coil 414. The resulting electric field 416 has a middle region that is less aggressively shaped and bent or curved slightly upward and inboard of the small upper region of the field.

At position 3 (right), the coil configuration 420 is configured with a minimal degree of overlap of the secondary coil 422 over the primary coil 424. In this configuration, an edge portion of the secondary coil 422 is aligned approximately with an edge portion of the primary coil 424. The resulting electric field 426 has a middle region that exhibits a minimal degree of shaping/bending.

From the above, it will be appreciated that the electric field produced by the stimulator 100 can be tailored by selecting the appropriate combination of coil characteristics. Increasing the number/diameter of coils increases the overall inductance of the stimulator, which increases the magnitude and penetration of the electric field. Increasing the overlap between the primary and secondary coils increases the shaping/bending of the field, at the expense of field penetration. Maximum shaping is achieved with maximum overlap, at the expense of penetration depth. Maximum penetration depth is achieved with no overlap and no deflection of the asymmetric field.

A good compromise amongst these considerations can be achieved where enough deflection is achieved to reduce the field on the off-target areas, while still maintaining enough penetration to insure proper stimulation at the target. By finding an appropriate combination of number of coils, coil positioning, and overlap, the stimulator can be adapted to produce an electric field that can hit the target while avoiding off-target areas. To facilitate selecting the degree of deflection/penetration, the housing 110 of the stimulator can be configured to allow the position of the secondary coil 144 to be adjusted relative to the primary coil 142. In this manner, the user can choose the "mode" of the coil, varying the degree of penetration and deflection.

What is claimed is:

1. An apparatus for providing deep nerve stimulation to a target area of a patient, comprising:
  a housing;
  a primary coil supported in the housing, the primary coil configured while being energized to produce a broad and deeply penetrating electric field capable of hitting the target area; and
  a secondary coil supported in the housing, the secondary coil being configured and arranged to, when energized, shape the field produced by the primary coil, wherein the secondary coil is configured and arranged so that a portion of the secondary coil overlaps a portion of the primary coil, wherein the housing comprises:
  a wall with an outer surface for being presented toward the target area, the primary coil being supported in a primary chamber of the housing adjacent an inner surface of the wall, opposite the outer surface; and
  ribs disposed between the primary coil and the inner surface and upon which the primary coil rests, the ribs defining channels through which coolant is directed to cool a bottom surface of the primary coil, the bottom surface of the primary coil being the surface of the primary coil positioned closest to the inner surface of the wall.

2. The apparatus recited in claim 1, wherein the secondary coil is configured and arranged to shape the field produced by the primary coil in a direction of an off-target area.

3. The apparatus recited in claim 1, wherein the overlap between the primary and secondary coils is adjustable so as to tailor the shaping effect that the secondary coil has on the field produced by the primary coil.

4. The apparatus recited in claim 1, wherein the primary coil and secondary coil are wound in series.

5. The apparatus recited in claim 1, wherein the primary coil and secondary coil are wound in opposite directions.

6. The apparatus recited in claim 1, comprising multiple secondary coils for shaping the field produced by the primary coil, wherein the secondary coils are arranged relative to each other and to the primary coil in a manner selected to shape the field produced by the primary coil.

7. The apparatus recited in claim 1, wherein positions of the secondary coils relative to each other is adjustable.

8. The apparatus recited in claim 1, wherein the housing comprises a hub around which the primary coil is wound, the hub defining a central conduit through which the coolant flows and is distributed to the channels to cool the primary coil.

9. The apparatus recited in claim 8, wherein the hub has a terminal end positioned on the ribs so as to space the terminal end away from the inner surface of the wall at locations between the ribs, the terminal end and the ribs defining apertures through which the coolant is directed into the channels from the conduit.

10. The apparatus recited in claim 8, wherein the ribs extend radially from the hub, thereby giving the channels a radial configuration, the coolant flowing from the hub radially outward over the primary coil.

11. The apparatus recited in claim 10, wherein the housing comprises an outer wall with a curved profile that directs radially flowing portions of the coolant over an opposite surface of the primary coil.

12. The apparatus recited in claim 11, further comprising coil clamps that connect with the housing to help maintain the position of the primary coil within the housing, the coil clamps extending radially from the hub to the outer wall and defining therebetween channels into which portions of the coolant directed from the outer wall flows radially over a top surface of the primary coil.

13. The apparatus recited in claim 1, wherein the housing comprises a fluid collecting chamber for collecting the coolant after it has flowed over the primary coil, and a bubble trap for collecting air bubbles that form in the coolant.

14. The apparatus recited in claim 1, wherein the secondary coil is configured for shaping the magnetic field generated by the primary coil, the secondary coil being disposed in a secondary chamber of the housing and at least partially overlying a top surface of the primary coil.

15. A method for using the apparatus recited in claim 1 to provide the deep nerve stimulation to the target area of the patient, comprising: utilizing the primary coil to produce, when energized, a broad and deeply penetrating magnetic field capable of hitting the target area; positioning the secondary coil relative to the primary coil in order to when energized shape the magnetic field produced by the primary coil; and positioning the secondary coil to overlap the portion of the primary coil.

16. The method recited in claim 15, further comprising positioning the secondary coil to shape the field produced by the primary coil in a direction of an off-target area.

17. The method recited in claim 15, further comprising adjusting the overlap between the primary and secondary coils to tailor the shaping effect that the secondary coil has on the field produced by the primary coil.

18. The method recited in claim 15, further comprising positioning multiple secondary coils relative to the primary coil in order to shape the field produced by the primary coil.

19. The method recited in claim 18, further comprising adjusting positions of the multiple secondary coils relative to each other in order to further shape the field produced by the primary coil.

* * * * *